United States Patent
Klassen et al.

(10) Patent No.: US 11,139,056 B2
(45) Date of Patent: *Oct. 5, 2021

(54) METHODS OF TREATING OVERWEIGHT AND OBESITY

(71) Applicant: Nalpropion Pharmaceuticals, LLC, Morristown, NJ (US)

(72) Inventors: Preston Klassen, La Jolla, CA (US); Kristin Taylor, San Diego, CA (US)

(73) Assignee: Nalpropion Pharmaceuticals LLC, Brentwood, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/558,211

(22) Filed: Sep. 2, 2019

(65) Prior Publication Data
US 2020/0098285 A1   Mar. 26, 2020

Related U.S. Application Data

(63) Continuation of application No. 15/491,870, filed on Apr. 19, 2017, now Pat. No. 10,403,170, which is a continuation of application No. 14/405,775, filed as application No. PCT/US2013/044368 on Jun. 5, 2013, now Pat. No. 9,633,575.

(60) Provisional application No. 61/656,451, filed on Jun. 6, 2012.

(51) Int. Cl.
| | |
|---|---|
| *G16H 20/10* | (2018.01) |
| *A61K 31/137* | (2006.01) |
| *A61K 31/485* | (2006.01) |
| *G01G 19/414* | (2006.01) |
| *A61P 9/04* | (2006.01) |
| *A61P 9/00* | (2006.01) |
| *A61P 9/10* | (2006.01) |
| *A61P 3/04* | (2006.01) |
| *G09B 5/06* | (2006.01) |
| *G09B 19/00* | (2006.01) |

(52) U.S. Cl.
CPC .......... *G16H 20/10* (2018.01); *A61K 31/137* (2013.01); *A61K 31/485* (2013.01); *A61P 3/04* (2018.01); *A61P 9/00* (2018.01); *A61P 9/04* (2018.01); *A61P 9/10* (2018.01); *G01G 19/4146* (2013.01); *G09B 5/065* (2013.01); *G09B 19/0092* (2013.01)

(58) Field of Classification Search
CPC .................................... A61K 31/485
USPC ................................. 514/282, 909
See application file for complete search history.

(56) References Cited

U.S. PATENT DOCUMENTS

| | | | |
|---|---|---|---|
| 8,969,371 B1 * | 3/2015 | Klassen | A61K 31/137 |
| | | | 514/282 |
| 9,119,850 B2 * | 9/2015 | Klassen | A61K 31/485 |
| 9,633,575 B2 * | 4/2017 | Klassen | A61K 31/137 |
| 9,801,875 B2 | 10/2017 | Klassen et al. | |
| 10,231,962 B2 | 3/2019 | Klassen et al. | |
| 10,231,964 B2 * | 3/2019 | Klassen | A61K 31/137 |
| 10,403,170 B2 * | 9/2019 | Klassen | A61K 31/485 |
| 10,828,294 B2 | 11/2020 | Klassen et al. | |
| 10,835,527 B2 | 11/2020 | Klassen et al. | |

FOREIGN PATENT DOCUMENTS

WO    WO-2009158114 A1 * 12/2009 .......... A63K 31/485

* cited by examiner

*Primary Examiner* — Kevin E Weddington
(74) *Attorney, Agent, or Firm* — Servilla Whitney LLC

(57) ABSTRACT

The present disclosure relates to compositions, kits, uses, systems and methods for treating overweight and obesity using naltrexone plus bupropion, preferably in combination with a comprehensive web-based and/or telephone-based weight management program, and preferably in subjects at increased risk of adverse cardiovascular outcomes.

15 Claims, No Drawings

METHODS OF TREATING OVERWEIGHT AND OBESITY

RELATED APPLICATIONS

The present application is a continuation of U.S. application Ser. No. 15/491,870, filed Apr. 19, 2017, which is a continuation of U.S. application Ser. No. 14/405,775, now U.S. Pat. No. 9,633,575, which is the U.S. National Phase under 35 U.S.C. § 371 of International Application No. PCT/US2013/044368, entitled "METHODS OF TREATING OVERWEIGHT AND OBESITY," filed Jun. 5, 2013, and published in English on Dec. 12, 2013 as WO 2013/184837, which is a non-provisional of and claims priority to U.S. Provisional Application No. 61/656,451 filed on Jun. 6, 2012, which, where permitted, is herein incorporated by reference in its entirety.

BACKGROUND

Field of the Invention

The present disclosure relates to compositions, kits, uses, systems and methods for treating overweight and obesity using naltrexone plus bupropion, preferably in combination with a comprehensive web-based and/or telephone-based weight management program, and optionally in subjects at increased risk of adverse cardiovascular outcomes.

Description of the Related Art

Obesity has been defined in terms of body mass index (BMI). BMI is calculated as weight $(kg)/[height\ (m)]^2$. According to the guidelines of the U.S. Centers for Disease Control and Prevention (CDC) and the World Health Organization (WHO), for adults over 20 years old, BMI is categorized as follows: below 18.5 is considered underweight, 18.5-24.9 is considered normal, 25.0-29.9 is considered overweight, and 30.0 and above is considered obese (World Health Organization. Physical status: The use and interpretation of anthropometry, Geneva, Switzerland: World Health Organization 1995. WHO Technical Report Series).

The prevalence of obesity has markedly increased over the past three decades, with 32% of men and 36% of women considered obese. These individuals are at increased risk for a variety of chronic conditions associated with obesity, including type 2 diabetes, coronary heart disease, hypertension, stroke, dyslipidemia, gallbladder disease, sleep apnea, certain types of cancer, and osteoarthritis, as well as increased mortality risk from all causes (NHLBI Clinical Guidelines, 1998). Overweight and obesity are also associated with increased all-cause mortality.

Diet and exercise-based behavioral modification is the mainstay of weight management therapy. However, such intervention is often of limited effectiveness and difficult for individuals to adhere to. Therefore, pharmacotherapy has been employed as an adjunct to diet and exercise. Orlistat, lorcaserin, and phentermine/topiramate are currently the only three drugs approved in the United States for the long-term treatment of obesity. A 5-10% weight loss has been determined to lead to significant medical benefits. While orlistat has a favorable safety profile, it can cause loose stools and fecal incontinence, making acceptance by patients difficult. Bariatric surgery (specifically gastric banding) is now indicated for subjects with BMI ≥30 kg/m2 who have at least one obesity-related comorbidity. While effective in most cases, it is invasive with possible complications including infection, death, hypoglycemia, failure to lose weight, gastrointestinal symptoms, nutritional deficiencies, depression, sexual and relationship problems, and noncompliance with behavioral recommendations.

U.S. Pat. Nos. 7,375,111 and 7,462,626 disclose the combination of naltrexone and bupropion (NB) for weight loss therapy. Wadden et al. disclose the combination of naltrexone and bupropion as an adjunct to an intensive behavioral modification (BMOD) program for weight loss. *Obesity* (2011) 19:110-120. The BMOD program described by Wadden et al. was delivered in person to groups of 10-20 persons. Group meetings lasted 90 min and were held weekly for the first 16 weeks, every other week for the next 12 weeks, and monthly thereafter (yielding a total of 28 sessions). Group sessions typically began with a review of participants' eating and activity records and other homework assignments. Group leaders then introduced a new topic in weight control which, during the first 16 weeks, included meal planning, stimulus control, slowing eating, problem solving, social support, and coping with high risk situations. Subsequent sessions covered skills required for maintaining lost weight.

While the combination of naltrexone and bupropion is known to be efficacious for weight management for some patient populations, alone or in combination with an intensive BMOD program, a need exists for an effective treatment of overweight or obesity in subjects at increased risk of adverse cardiovascular outcomes. In addition, there exists a need for a weight management program for use in combination with naltrexone and bupropion that is easier for patients to comply with than existing BMOD programs, but which is still efficacious, particularly in subjects at increased risk of adverse cardiovascular outcomes.

SUMMARY

An embodiment of the invention includes a method of treating a subject at increased risk of an adverse cardiovascular outcome comprising for overweight or obesity: identifying an overweight or obese subject at increased risk of an adverse cardiovascular outcome; and administering to the subject a therapeutically effective amount of sustained release naltrexone, or a pharmaceutically acceptable salt thereof, and sustained release bupropion, or a pharmaceutically acceptable salt thereof. In some embodiments, aid overweight or obese subject is identified as being at increased risk of an adverse cardiovascular outcome if the subject: a.) is diagnosed as having cardiovascular disease with at least one risk factor selected from the group consisting of: a history of documented myocardial infarction >3 months prior to the identification; a history of coronary revascularization including coronary artery bypass graft surgery, stent placement, percutaneous transluminal coronary angioplasty, or laser atherectomy; a history of carotid or peripheral revascularization, including carotid endarterectomy, lower extremity atherosclerotic disease atherectomy, repair of abdominal aorta aneurysm, femoral or popliteal bypass; angina with ischemic changes, ECG changes on a graded exercise test, or positive cardiac imaging study; ankle brachial index <0.9 assessed by simple palpation within prior 2 years of the identification; and ≥50% stenosis of a coronary, carotid, or lower extremity artery within prior 2 years of the identification; and/or b.) is diagnosed as having Type 2 diabetes mellitus with at least 2 risk factors selected from the group consisting of: hypertension controlled with or without pharmacotherapy at <145/95 mm Hg;

dyslipidemia requiring pharmacotherapy; documented low HDL cholesterol, <50 mg/dL in women or <40 mg/dL in men, within prior 12 months of the identification; and current tobacco smoker.

In some embodiments, the method further comprises a lead-in 2-week period during which the subject receive treatment according to one of two sequences: 1 week of active study medication comprising sustained release naltrexone, or a pharmaceutically acceptable salt thereof, and sustained release bupropion, or a pharmaceutically acceptable salt thereof, once a day followed by 1 week of placebo once a day; or 1 week of placebo followed by 1 week of active study medication comprising sustained release naltrexone, or a pharmaceutically acceptable salt thereof, and sustained release bupropion, or a pharmaceutically acceptable salt thereof.

In some embodiments, the subject does not have one or more characteristics selected from the group consisting of: myocardial infarction within 3 months prior to the identification; angina pectoris Grade III or IV as per the Canadian Cardiovascular Society grading scheme; a clinical history of cerebrovascular disease including stroke; a history of tachyarrhythmia other than sinus tachycardia; blood pressure ≥145/95 mm Hg, irrespective of treatment with antihypertensive agents; unstable weight within 3 months prior to the identification; planned bariatric surgery, cardiac surgery, or coronary angioplasty; severe renal impairment defined by an estimated GFR <30 mL/min; clinical history of liver failure or documented ALT or AST greater than 3 times the upper limit of normal; known infection with HIV or hepatitis; chronic use or positive screen for opioids; recent drug or alcohol abuse or dependence, with the exception of nicotine dependence, within 6 months prior to the identification; history of seizures, including febrile seizures, cranial trauma, or other conditions that predispose the subject to seizures; history of mania or current diagnosis of active psychosis, active bulimia or anorexia nervosa, but not binge eating disorder; a risk for suicide attempts; acute depressive illness including new onset of depression or acute exacerbation of symptoms, but not stable subjects on chronic treatment for depression; any condition with life expectancy anticipated to be less than 4 years including congestive heart failure NYHA Class 3 or 4; a history of malignancy within the previous 5 years, not including non-melanoma skin cancer or surgically cured cervical cancer; current use of other bupropion or naltrexone containing products; a history of hypersensitivity or intolerance to naltrexone or bupropion; use of monoamine oxidase inhibitors within 14 days prior to the identification; use of any investigational drug, device, or procedure within 30 days prior to the identification; a pregnant or breast-feeding woman, or currently trying to become pregnant, or of child-bearing potential, including peri-menopausal women who have had a menstrual period within one year, and not willing to practice birth control; and inability to consistently access broadband internet.

In some embodiments, the method further comprises providing the subject with a web-based weight management program, a phone-based weight management program, or a combination thereof.

An embodiment of the invention includes a method of treating a subject for overweight or obesity comprising: identifying an overweight or obese subject; and administering to the subject a therapeutically effective amount of sustained release naltrexone, or a pharmaceutically acceptable salt thereof, and sustained release bupropion, or a pharmaceutically acceptable salt thereof, in combination with a web-based weight management program, a phone-based weight management program, or a combination thereof.

In some embodiments, the identified subject has a BMI ≥30 and ≤45 kg/m2 with uncomplicated obesity. In some embodiments, the identified subject has a BMI of ≥27 and ≤45 kg/m2 with dyslipidemia and/or controlled hypertension. In some embodiments, the subject is treated for at least 26 weeks. In some embodiments, the phone-based weight management program comprise one or more coaching calls to the subject. In some embodiments, the phone-based weight management program optionally comprises one or more web coaching tools. In some embodiments, the web-based or phone-based weight management program provides the subject with one or more of behavioral, nutritional or fitness education.

In some embodiments, the education are delivered by a trained health or fitness coach and/or a registered dietitian. In some embodiments, the trained health or fitness coach and/or the registered dietitian counsel the subject via the phone or via a website for the subject, and provide one or more of the topics selected from the group consisting of tips and motivational messages; coaching through question and answer; weekly office hours for real-time responses to the subject's inquiries via the website; weekly educational materials; video lessons; weight, exercise, or diet tracking with badge rewards; goal setting; progress tracking; and communications to encourage the subject to engage in the weight management program.

In some embodiments, 32 mg per day of sustained release naltrexone, or a pharmaceutically acceptable salt thereof, and 360 mg per day of sustained release bupropion, or a pharmaceutically acceptable salt thereof, is administered to the subject. In some embodiments, the subject is administered the sustained release naltrexone, or a pharmaceutically acceptable salt thereof, and the sustained release bupropion, or a pharmaceutically acceptable salt thereof, in a tablet containing 8 mg of sustained release naltrexone and 90 mg of sustained release bupropion.

In some embodiments, the treatment with naltrexone and bupropion does not increase the subject's risk of an adverse cardiovascular outcome. In some embodiments, the treatment with naltrexone and bupropion decreases the subject's risk of an adverse cardiovascular outcome. In some embodiments, the adverse cardiovascular outcome is cardiovascular death, nonfatal myocardial infarction, or nonfatal stroke. In some embodiments, the subject achieves a percentage of weight loss of at least 5%, at least 10% or at least 15%. In some embodiments, the weight management program has a period of at least 52 weeks or at least 78 weeks.

In some embodiments, the subject does not receive in-person counseling as part of a weight management program. In some embodiments, the subject does not receive more than 5 in-person counseling sessions as part of a weight management program. In some embodiments, the subject does not receive an intensive behavioral modification (BMOD) program for weight loss.

DETAILED DESCRIPTION

The present disclosure relates to compositions, kits, uses, systems and methods for treating overweight and obesity using naltrexone plus bupropion, preferably in combination with a comprehensive lifestyle intervention (CLI) program including a web-based weight management program, a phone-based weight management program, and a combination thereof. In some embodiments, the subject being treated for overweight and obesity are subjects at increased risk of adverse cardiovascular outcomes. In a preferred embodiment, the treatment of a subject at increased risk of adverse cardiovascular outcomes with naltrexone plus bupropion in combination with a comprehensive web-based and/or telephone-based weight management program results in no more major adverse cardiovascular outcomes than treatment with the web-based and/or telephone-based weight management program alone. In some embodiments, the treatment of a subject at increased risk of adverse cardiovascular outcomes with naltrexone plus bupropion in combination with a comprehensive web-based and/or telephone-based weight management program surprisingly results in fewer major adverse cardiovascular outcomes than treatment with the web-based and/or telephone-based weight management program alone. Major adverse cardiovascular outcomes are cardiovascular death (including fatal myocardial infarction and fatal stroke nonfatal myocardial infarction, nonfatal stroke, or nonfatal unstable angina requiring hospitalization.

In some embodiments, the subject being treated by the methods disclosed herein is at increased risk of adverse cardiovascular outcomes. Subjects at increased risk of adverse cardiovascular outcomes include subjects having a.) cardiovascular disease (confirmed diagnosis or at high likelihood of cardiovascular disease) with at least one of the following: history of documented myocardial infarction >3 months prior to screening; history of coronary revascularization (i.e., coronary artery bypass graft surgery, stent placement, percutaneous transluminal coronary angioplasty, or laser atherectomy); history of carotid or peripheral revascularization (i.e., carotid endarterectomy, lower extremity atherosclerotic disease atherectomy, repair of abdominal aorta aneurysm, femoral or popliteal bypass); angina with ischemic changes (resting ECG), ECG changes on a graded exercise test (GXT), or positive cardiac imaging study; ankle brachial index <0.9 (by simple palpation) within prior 2 years; ≥50% stenosis of a coronary, carotid, or lower extremity artery within prior 2 years; and/or b. Type 2 diabetes mellitus with at least 2 of the following: hypertension (controlled with or without pharmacotherapy at <145/95 mm Hg); dyslipidemia requiring pharmacotherapy; documented low cholesterol (<50 mg/dL in women or <40 mg/dL in men) within prior 12 months; current tobacco smoker.

In some such embodiments, the subject being treated has uncomplicated obesity. In some other embodiments, the subject being treated is overweight and has dyslipidemia and/or controlled hypertension. In some embodiments, the subject being treated by the methods disclosed herein is not at increased risk of adverse cardiovascular outcomes.

In some embodiments the treatment with naltrexone and bupropion is combined with a weight management program. In some embodiments, the weight management program is a web-based program. In some other embodiments, the weight management program is a phone-based program. In some other embodiments, the weight management program is a combination of both web-based and phone based programs. In some embodiments, the subject does not receive more than 15, 10, 5, 4, 3, 2, or 1 in-person counseling sessions as part of a weight management program. In some embodiments, the subject does not receive any in-person counseling sessions as part of a weight management program.

Web-Based Weight Management Program

Preferably, the web-based program provides a progressive nutrition and exercise program with goal setting and tracking tools. Each subject is assigned to a health and fitness professional who counsels them online throughout the program. Additional educational tools include weekly web-based informational, educational and motivational resources supplemented by video lessons (Table 1) presented at regular intervals. Content for the program consists of: a weekly email that announces the goals for the week, provides motivation, and encourages continued participation; weekly goals (from email) that align with each week's theme (Table 1), along with a detailed explanation and a strategy for achieving these goals, placed on the MyWeightMate.com subject pages; three pieces of additional weekly content posted to user pages (tips and educational information) to help subjects reach their weekly goals; motivational messages throughout the week posted on participant pages; triggered event emails sent to users based on behaviors (i.e. absence from program activity, successful logging); video lessons provided on the MyWeightMate.com site for participants to view and archived for future access: weekly for the first 16 weeks, biweekly for the next 12 weeks, monthly for the remaining duration of the study, and two refresher campaigns that include 4 weekly sessions each year during the third and fourth year of the trial. Video lessons focus on relevant topics and are developed by subject matter experts.

TABLE 1

Weekly Themes and Video Topics for First 16 Weeks of the Weight Management Program

| Week | Theme | Video Lesson Topic |
|---|---|---|
| 1 | Get Started | Setting Yourself Up For Success: Getting Your Mind Right |
| 2 | Perfect Portions | SMART Goals |
| 3 | Avoid Pitfalls | Proper Form When You Move |
| 4 | Get More Vitamin Zzz | Healthful Substitutions for Food and Exercise |
| 5 | Boost Your Fitness | Fitness Myths |
| 6 | Skinny Food Secrets | Smart Strategies for Eating Less |
| 7 | Smash Sugar Spikes | How Do You Make Time For Your Health and Why is It Psychologically Important? |
| 8 | Take the Show on the Road | Accidental Exercise |
| 9 | Take Some Pressure Off | Powering Up Your Exercise |
| 10 | Metabolism Superchargers | Staying Fit If You Sit |
| 11 | Clobber High Cholesterol | Healthy Choices |
| 12 | Motivation Boosters | Breaking Weight Loss Plateaus |
| 13 | Kick It up | Replacing Bad Habits With Healthy Ones |
| 14 | Rut Busters | The Diet Hype Trap |

TABLE 1-continued

Weekly Themes and Video Topics for First 16 Weeks of the Weight Management Program

| Week | Theme | Video Lesson Topic |
|---|---|---|
| 15 | Shore Up Your Self-Confidence | Healthy Living Guide: Live Your Best Life |
| 16 | Review and Renew | Boost Your Metabolism |

The web-based weight management program provides behavioral, nutritional and fitness education delivered by trained health and fitness coaches. The website provides a "WeightMate Coach" who counsels the subject via the participant's individual webpage, and provides one or more of the following: tips and motivational messages; coaching through Q&A; weekly office hours for real-time response via the website; weekly educational materials; content developed with subject matter experts; video lessons to supplement the weekly themes; weight, exercise, and diet tracking with badge rewards; suggested activity and coaching tip; communication to encourage engagement; and a contemporary website that is fin and intuitive.

In one embodiment, new themes and goals are introduced each Monday, with 2-3 goals of the week, relevant content and/or video lesson(s) (Table 1) are provided, and motivational messages are provided on one or more days of the week. Optionally, additional tips are provided one or more days during the week. In some embodiments, video lessons supplement the weekly educational themes. The produced video content ensures quality and uniformity of message to subjects, and a Q&A function allows patients to ask questions with <24 hour turnaround.

In some embodiments, web-based individual counseling is provided by a coach; preferably the subject has unlimited access to coach. Preferably the coach provides a schedule to the subject which includes weekly 'office hours' for real-time Q&A responses. The program emphasizes weekly weigh ins with daily food and activity tracking. Preferably, the website can track calories for each meal using a computer database of calories for specific foods and/or meals, and save favorite foods and meals. Four reference menus based on caloric needs and food preferences are provided. In some embodiments the subject is rewarded with badges for meeting particular goals (e.g., for 7 days of activity logged; for 7 days of food logged; for 3 weeks of weight logged; for first 15 pounds lost; for 12 weeks of program participation; for 26 weeks of program participation; for 52 weeks of program participation; for 78 weeks of program participation; for 5% weight loss; for 10% weight loss; for 15% weight loss). In a preferred embodiment, the subject periodically establishes a weight loss goal which is recorded as part of the program. The subject's progress toward the subject's goal(s) can be provided to the subject via the subject's webpage. The weight loss goal can be the goal for a one week, two week, month, two month, six month, year or longer period of time. The program provides the option for the participating subject to set a specific weight loss goal at the beginning of the program. The program also provides the option to track and log weight loss, and the progress towards achieving the specific goal on a daily or weekly basis. Optionally, a graphic representation of weight loss progress is provided to the subject via the subject's webpage. Periodic encouraging messages (e.g., badges and award notes) can be provided. Preferably, behavior-based automated messages from trainers are provided for increased motivation and participation.

In some embodiments, the exercise portion of the web-based weight management program encourages 5 days of activity and 2 days of rest, preferably on non-consecutive days (e.g. Monday and Friday). In some embodiments, the exercise program provides instructions on stretching, walking and other light cardio activity. Video clips can provide educational demonstration for stretches and exercise maneuvers. The website can track calories burned by the subject through exercise and activity logs.

In a preferred embodiment, the web-based weight management program does not involve any in-person therapy or group meetings.

Phone-Based Weight Management Program

In some embodiments, the telephone-based program comprises personalized coaching through one or more phone calls. In one embodiment, the phone calls are conducted by a dedicated coach to the subject receiving treatment. In another embodiment, the phone calls are conducted by a registered dietitian to the subject receiving treatment. In some such embodiments, the phone-based program includes 6 to 15, preferably 12 scheduled calls over the first 3 to 8, preferably 6 months of the treatment. The topics of said scheduled calls can include cognitive behavioral coaching and nutrition coaching (See, for example, Table 2). In some such embodiments, the phone-based program includes 6 to 15, preferably 12 additional calls over the next 3 to 8, preferably 6 months of treatment.

In some embodiments, the phone-based program optionally comprises on-line coaching tools, such as an integrated web support for web coaching, including the web-based program described above. The web coaching can include the essential practices for weight loss and maintaining weight loss, progress tracking, and/or virtual coaching. Non-limiting examples of the essential practices can include E-lessons, videos and podcasts, articles and games relating to topics such as healthy cooking, setting realistic goals, and controlling stress. Non-limiting examples of items the progress trackers can track include weight, nutrition intake, activity, stress, biometrics, coaching calls, etc. Non-limiting example of virtual coating can include generating and updating of to-do list for a subject participating in the program, sending emails, etc.

In some embodiments, the phone-based program can also optionally include one or more electronic devices for wireless activity monitoring. Non-limiting example of such electronic device is FitLinxx®ActiPed to be used in conjunction with a USB access point to track steps, distance, calories and activity time. The electronic device(s) can be wirelessly synced with the web support. In one embodiment, the phone-based program is the Weight Talk® Program available from Alere™.

A subject receiving the treatment of naltrexone and bupropion can enroll in the phone-based program via various methods, including both web enrollment and phone enrollment. In some embodiments, the phone-based program also include frontline support to identify patients who qualify for the clinical study, discuss benefit of the phone-based program, set realistic expectations, assist in enrollment and refer specific question to coaches.

TABLE 2

Exemplary Phone-based Weight Management Program Call Topics

| Call # | Call Topics |
|---|---|
| Call 1: | Getting Started: Core Values, goal setting and tracking |
| Call 2: | Reducing calories and healthy eating (with registered dietitian) |
| Call 3: | Increasing physical activity |
| Call 4: | Managing stress |
| Call 5: | Changing unhelpful thoughts |
| Call 6: | Gaining control of your environment (with registered dietitian) |
| Call 7: | Developing time management skills and improving sleep |
| Call 8: | Navigating difficult situations: social situations and restaurants |
| Call 9: | Weight maintenance skills |
| Call 10: | Rebounding from lapses |
| Call 11: | Maintaining motivation |
| Call 12: | Evaluation and Participant Feedback |

In a preferred embodiment, treatment with a combination of naltrexone sustained-release (SR)/bupropion SR (NB), alone or in conjunction with a web-based and/or telephone-based weight management program, does not increase, or more preferably decreases, the occurrence of major adverse cardiac events, defined as cardiovascular death, nonfatal myocardial infarction, or nonfatal stroke in overweight and obese subjects, as compared to placebo or a web-based and/or telephone-based weight management program alone. In some embodiments, treatment with NB, alone or in conjunction with a web-based and/or telephone-based weight management program, does not increase, or more preferably decreases, the occurrence of one or more of cardiovascular death, nonfatal myocardial infarction, nonfatal stroke, or nonfatal unstable angina requiring hospitalization in overweight and obese subjects, as compared to placebo or a web-based and/or telephone-based weight management program alone. In some embodiments, treatment with NB, alone or in conjunction with a web-based and/or telephone-based weight management program, does not increase, or more preferably decreases, one or more of: the occurrence of all cause mortality; the occurrence of unstable angina requiring hospitalization; and the occurrence of coronary revascularization procedures, as compared to placebo or a web-based and/or telephone-based weight management program alone. In some embodiments, treatment with NB, alone or in conjunction with a web-based and/or telephone-based weight management program, decreases body weight or improves systolic and/or diastolic blood pressure, as compared to placebo or a web-based and/or telephone-based weight management program alone. In some embodiments, the individual treated is overweight or obese, and at increased risk of adverse cardiovascular outcomes.

In some embodiments, treatment with a combination of naltrexone sustained-release (SR)/bupropion SR (NB), alone or in conjunction with a web-based and/or telephone-based weight management program, increases one or more of: the percent change in body weight from baseline; the percentage of subjects achieving a loss of at least 5%, 10%, and 15% of baseline body weight; and the absolute change in body weight from baseline, compared to Usual Care (no study medication and minimal lifestyle intervention program). In some embodiments, treatment with NB, alone or in conjunction with a web-based and/or telephone-based weight management program, improves one or more of: cardiovascular risk factors (one or more of waist circumference, fasting triglycerides, fasting LDL cholesterol, and fasting HDL cholesterol); vital signs (one or more of systolic and/or diastolic blood pressure, and heart rate); measures of glucose metabolism (one or more of fasting glucose, fasting insulin, and HOMA-IR); measurements derived from patient reported outcomes (one or more of eating behavior (e.g. BES), sexual function (e.g. ASEX Scale), and weight-related quality of life (e.g. IWQOL-Lite)), as compared to Usual Care (no study medication and minimal lifestyle intervention program). In some embodiments, the above mentioned increases or improvements are measured at week 26 of treatment in comparison to baseline, in some embodiments the measurements are at week 52 or 78 of treatment in comparison to baseline. In some embodiments that treated individual is female or male, 18 to 60 years, inclusive, of age, with a BMI ≥30 and ≤45 kg/m$^2$ for subjects with uncomplicated obesity, and a BMI of ≥27 and ≤45 kg/m$^2$ for subjects who are overweight or obese and have dyslipidemia and/or controlled hypertension. In some embodiments the treated individual is overweight or obese, and at increased risk of adverse cardiovascular outcomes. In some embodiments, the treated individual is not overweight or obese, and at increased risk of adverse cardiovascular outcomes.

In some embodiments, treatment with a combination of naltrexone sustained-release (SR)/bupropion SR (NB), in conjunction with a web-based and/or telephone-based weight management program, is the same or increases one or more of: the percent change in body weight from baseline; the percentage of subjects achieving a loss of at least 5%, 10%, and 15% of baseline body weight; and the absolute change in body weight from baseline, compared to NB in conjunction with an intensive behavioral modification (BMOD) program for weight loss delivered in person. In some embodiments, treatment with NB, alone or in conjunction with a web-based and/or telephone-based weight management program, is the same or improves one or more of: cardiovascular risk factors (one or more of waist circumference, fasting triglycerides, fasting LDL cholesterol, and fasting HDL cholesterol); vital signs (one or more of systolic and/or diastolic blood pressure, and heart rate); measures of glucose metabolism (one or more of fasting glucose, fasting insulin, and HOMA-IR); measurements derived from patient reported outcomes (one or more of eating behavior (e.g. BES), sexual function (e.g. ASEX Scale), and weight-related quality of life (e.g. IWQOL-Lite)), as compared to NB in conjunction with an intensive behavioral modification (BMOD) program for weight loss delivered in person. In some embodiments, the above mentioned increases or improvements are measured at week 26 of treatment in comparison to baseline, in some embodiments the measurements are at week 52 or 78 of treatment in comparison to baseline. In some embodiments that treated individual is female or male, 18 to 60 years, inclusive, of age, with a BMI ≥30 and ≤45 kg/m$^2$ for subjects with uncomplicated obesity, and a BMI of ≥27 and ≤45 kg/m$^2$ for subjects who are overweight or obese and have dyslipidemia and/or controlled hypertension. In some embodiments the treated individual is overweight or obese, and at increased risk of adverse cardiovascular outcomes. In some embodiments, the treated individual is not overweight or obese, and at increased risk of adverse cardiovascular outcomes.

In some embodiments, the individual has a body mass index (BMI) of at least 25 kg/m$^2$. In some embodiments, the individual has a Mill of at least 30 kg/m$^2$. In some embodiments, the individual has a BMI of at least 40 kg/m$^2$. In some embodiments, the individual has a BMI of less than 25 kg/m$^2$, or develops a BMI less than 25 kg/m$^2$ during the course of administration of naltrexone and bupropion. In these embodiments, it may be beneficial for health or cosmetic purposes to mitigate subsequent weight gain or to promote weight loss, thereby reducing the BMI even further. In some embodiments, the individual has been diagnosed by a physician as being overweight or obese. In some embodiments, the individual is identified, including self-identified, as overweight or obese, or is identified as having been diagnosed as overweight or obese. In some embodiments, the individual is suffering from dyslipidemia and/or controlled hypertension in addition to being overweight, or in addition to being obese.

In some embodiments, the promotion of weight loss is measured by a percent change from a baseline body weight. In some of these embodiments, the amount of weight loss is, is about, is at least, is at least about 0.5%, 1%, 1.5%, 2%, 2.5%, 3%, 4%, 5%, 6%, 7%, 8%, 9%, 10%, 12%, 15%, or more of initial body weight, or a range defined by any two of the preceding values. In some embodiments, the promotion of weight loss is measured as a reduction in weight gain relative to the amount of weight gain experienced by the relevant control, and the amount of reduction in weight gain is, is about, is at least, is at least about, 2%, 5%, 10%, 15%, 20%, 25%, 30%, 40%, 50%, 60%, 70%, 80%, 90%, 100%, 105%, 110%, 115%, 120%, or more, or a range defined by any two of the preceding values.

In some embodiments, the dosage is adjusted so that the patient loses weight at a rate of about 3% of baseline body weight every six months. However, the rate of weight loss for a patient may be adjusted by the treating physician based on the patient's particular needs.

In some embodiments, the mitigation of weight gain or promotion of weight loss occurs by increasing satiety in the individual. In some embodiments, the mitigation of weight gain or promotion of weight loss occurs by suppressing the appetite of the individual. In some embodiments, the treatment comprises instituting a regimen of diet and/or increased activity.

In some embodiments, the naltrexone or combination therapy, including naltrexone in combination with bupropion or fluoxetine, is in an amount sufficient to affect weight loss, reduce a cardiovascular risk factor, increase insulin sensitivity, reduce food cravings, treat a visceral fat condition, mitigate weight gain or promote weight loss during smoking cessation, or provide weight loss therapy in patients with major depression. Non-limiting examples of such methods of treatment are disclosed in U.S. Pat. Nos. 7,375,111 and 7,462,626; in U.S. Patent Publication Nos. 2007/0275970, 2007/0270450, 2007/0117827, 2007/0179168, 2008/0214592, 2007/0128298, and 2007/0129283; in U.S. patent application Ser. Nos. 12/751,970, 61/167,486, and 61/293,844; and in WO 2009/158114, each of which is hereby incorporated herein by reference in their entirety and for all purposes, including without limitation for the purpose of describing methods of affecting weight loss, reducing cardiovascular risk factors, increasing insulin sensitivity, reducing food cravings, treating visceral fat conditions, mitigating weight gain or promoting weight loss during smoking cessation, and providing weight loss therapy in patients with major depression. In some embodiments, the cardiovascular risk factor includes one or more of the following: total cholesterol level, LDL cholesterol level, HDL cholesterol level, triglyceride level, glucose level, and insulin level. In some embodiments, the cardiovascular risk factor includes one or more of the following: total cholesterol level, HDL cholesterol level, and triglyceride level.

In some embodiments, the increased efficacy of a weight loss treatment described herein comprises an improvement in an outcome measure. For example, in some embodiments, the increased efficacy increases the amount of weight loss. In some embodiments, the increase in efficacy decreases the frequency or severity of adverse events, including but not limited to nausea, constipation, vomiting, dizziness, dry mouth, headache, and insomnia. In some embodiments, the increased efficacy improves another secondary endpoint, including but not limited to waist circumference, high-sensitivity C-reactive protein (hs-CRP) levels, triglyceride levels, HDL cholesterol levels or the ratio of LDL/HDL cholesterol levels. As one of skill in the art recognizes, in some circumstances, it is desirable to decrease waist circumference, hs-CRP levels, triglyceride levels, and the ratio of LDL/HDL cholesterol levels, and to increase HDL cholesterol levels. In some embodiments, the improvement in the outcome measure is, is about, is at least, or is at least about 1, 2, 3, 4, 5, 7, 10, 12, 15, 20 30, 40, 50, 60, 70, 80, 90, or 100%, or within a range defined by any two of these values as compared to baseline or the relevant control.

In some embodiments, naltrexone or naltrexone and bupropion are each administered once per day. In some embodiments, naltrexone and bupropion are each divided into equal doses and administered more than once per day. In some embodiments, naltrexone and bupropion are each divided into unequal doses and administered more than once per day. In some embodiments, naltrexone and bupropion are divided into a different number of doses and are administered a different number of times per day. In one such embodiment, the dose of one of naltrexone or bupropion is divided, while the dose of the other is not.

In some embodiments, one or both of naltrexone and bupropion is administered one, two, three, four, or more times per day. Either or both compounds can be administered less than once per day, for example once every 2, 3, 4, 5, 6, 7, 8, 9, 10, 11, 12, 13, or 14 days, or every 1 or 2 weeks, or a range defined by any two of ceding values. In some embodiments, the number of administrations per day is constant (e.g., one time per day). In other embodiments, the number of administrations is variable. The number of administrations may change depending on effectiveness of the dosage form, observed side effects, external factors (e.g., a change in another medication), or the length of time that the dosage form has been administered.

In some embodiments, the daily dose of naltrexone can range from about 4 mg to about 50 mg, or about 4 mg to about 32 mg, or about 8 mg to about 32 mg, or about 8 mg to about 16 mg. In some embodiments, the daily dose is about 4 mg, about 8 mg, about 12 mg, about 16 mg, about 32 mg, or about 48 mg of naltrexone, or a range defined by any two of the preceding values. The selection of a particular dosage may be based on the weight of the patient. The selection of a particular dosage may be based on the identity, dosage, and/or dosing schedule of another co-administered compound. However, in some embodiments, it may be necessary to use dosages outside these ranges. In some embodiments, the daily dose is administered in a single oral dosage form. In some embodiments, the daily dose of naltrexone is the same, and in some embodiments, the daily dose is different.

In some embodiments, the daily dose of bupropion can range from about 30 mg to about 500 mg, or about 30 mg to about 360 mg, or about 90 mg to about 360 mg. In some embodiments, the daily dose is about 30 mg, about 90 mg, about 180 mg, about 360 mg, or about 450 mg of bupropion, or a range defined by any two of the preceding values. The selection of a particular dosage may be based on the weight of the patient. The selection of a particular dosage may be based on the identity, dosage and/or dosing schedule of another co-administered compound. However, in some embodiments, it may be necessary to use dosages outside these ranges. In some embodiments, the daily dose is administered in a single oral dosage form. In some embodiments, the daily dose of bupropion is the same, and in some embodiments, the daily dose is different.

The compositions described herein may be distributed, provided to a patient for self-administration, or administered to an individual. In some embodiments, the combined naltrexone/bupropion therapies include a third compound.

In some embodiments, naltrexone and/or bupropion are provided or administered as an oral dosage form. In some embodiments, the oral dosage form is in the form of a pill, tablet, core, capsule, caplet, loose powder, solution, or suspension. In a preferred embodiment, the oral dosage form is in the form of a pill, tablet, or capsule. In some embodiments, the combined naltrexone/bupropion therapy is provided in a single oral dosage form. In some embodiments, the oral dosage form is in the form of a trilayer tablet as described in U.S. Patent Publication No. 2008/0113026, which is incorporated herein by reference in its entirety and for all purposes, including without limitation for the purpose of describing trilayer tablets, methods of making and formulating trilayer tablets, and methods of administering them.

In some embodiments, at least one of naltrexone and bupropion is administered with varying frequency during treatment. In some of these embodiments, the varying frequency comprises a decreased frequency over time. For example, one or both of naltrexone and bupropion can be initially administered more than once per day, followed by administration only once per day at a later point in treatment. In some embodiments, the daily dosage of at least one of naltrexone and bupropion is consistent despite the varying frequency of administration. For example, in some embodiments, two tablets of each of naltrexone and bupropion are initially administered twice per day, while four tablets of each of naltrexone and bupropion are administered once per day at a later point in treatment. Alternatively, in some embodiments, one or two tablets of each of naltrexone and bupropion are administered at a later point in treatment, where the one or two tablets have an equivalent total daily dosage as the two tablets each of naltrexone and bupropion initially administered twice per day.

In some embodiments where one or both of naltrexone and bupropion are administered less than once per day in a controlled release or sustained release (SR) formulation, the dose is selected so that the patient receives a daily dose that is about the same as a daily dose described herein.

In some embodiments, the naltrexone, alone or in a combination treatment, is not a sequestered form of naltrexone. For example, in some embodiments, naltrexone is in a non-sequestered, controlled release formulation. In some embodiments, naltrexone is a non-sequestered, sustained release formulation. In preferred embodiments, at least 50% of the naltrexone is released within 24 hours of administration.

In some embodiments, at least one of naltrexone or bupropion is administered in consistent daily dosages throughout the period of treatment. In some embodiments, at least one of naltrexone or bupropion is administered in varying daily dosages during the period of treatment. In some of these embodiments, the daily dosages comprise increasing daily dosages over time. In some of these embodiments, the daily dosages comprise decreasing daily dosages over time.

In some embodiments, naltrexone and bupropion are administered individually. In some embodiments, naltrexone and bupropion are administered in a single pharmaceutical composition comprising naltrexone and bupropion. In some embodiments, at least one of naltrexone or bupropion is in a sustained release or controlled release formulation. For example, sustained release forms of naltrexone are described in U.S. Patent Publication No. 2007/0281021, which is incorporated herein by reference in its entirety and for all purposes, including without limitation for the purpose of describing sustained release forms of naltrexone and bupropion, methods of making and formulating them into suitable dosage forms, and methods of administering them. In some embodiments, at least one of naltrexone or bupropion is administered with a physiologically acceptable carrier, diluent, or excipient, or a combination thereof. Non-limiting examples of naltrexone/bupropion combinations, formulations thereof, and methods of administering them are disclosed in U.S. Pat. Nos. 7,375,111 and 7,462,626, both of which are incorporated herein by reference in their entirety and for all purposes, including without limitation for the purpose of describing combinations of naltrexone and bupropion, methods of making and formulating them into suitable dosage forms, and methods of administering them. Reference herein to the use or administration of naltrexone and naltrexone/bupropion combinations is understood to include all modes of administration disclosed or referred to herein, including without limitation separate administration, administration in a single dosage form, administration in the form of salts, and/or metabolites, and/or administration in sustained release forms. Techniques for formulation and administration of the compounds of the instant application may be found in "Remington's Pharmaceutical Sciences," Mack Publishing Co., Easton, Pa., 18th edition, 1990, which is incorporated herein by reference in its entirety.

In some embodiments, naltrexone is administered prior to bupropion. In some embodiments, naltrexone is administered subsequent to bupropion. In some embodiments, naltrexone and bupropion are co-administered. As used herein, co-administration includes administration in a single dosage form, or separate dosage forms that are administered at, or nearly at, the same time.

In some embodiments, the administration of naltrexone and bupropion is continued for a period of, or of about, 1, 2, 3, 4, 6, 8, 10, 12, 16, 20, 24, 36, 48, or 52 weeks, or a range defined by any two of the preceding values. In some embodiments, the administration of naltrexone and bupropion is continued until the reduction in symptoms of a disease, disorder, or condition is stabilized for a period of, or of about, 1, 2, 3, 4, 5, 6, or more weeks, or a range defined by any two of the preceding values. For example, in some embodiments, the administration of a combined naltrexone/bupropion therapy is continued until the mitigation of weight gain or promotion of weight loss in an individual is stabilized for a period of, or of about, 1, 2, 3, 4, 5, 6, or more weeks, or a range defined by any two of the preceding values. In some embodiments, administration of naltrexone, or naltrexone and bupropion, is continued until the individual no longer needs a treatment.

In some embodiments, "administering" a drug includes an individual obtaining and taking a drug on their own. For example, in some embodiments, an individual obtains a drug from a pharmacy and self-administers the drug in accordance with the methods provided herein.

In some embodiments, the present invention relates to a kit. The kit may include one or more unit dosage forms comprising naltrexone, bupropion, or naltrexone and bupropion. The unit dosage forms may be of an oral formulation. For example, the unit dosage forms may comprise pills, tablets, or capsules. The kit may include a plurality of unit dosage forms. In some embodiments, the unit dosage forms are in a container. In some embodiments, the dosage forms are single oral dosage forms comprising naltrexone and bupropion or pharmaceutically acceptable salts thereof.

The methods, compositions and kits disclosed herein may include information. The information may be in a form prescribed by a governmental agency regulating the manufacture, use, or sale of pharmaceuticals, which notice is reflective of approval by the agency of the form of the drug for human or veterinary administration. Such information, for example, may be the labeling approved by the U.S. Food and Drug Administration for prescription drugs, or the approved product insert. The information can include required information regarding dose and dosage forms, administration schedules and routes of administration, adverse events, contraindications, warning and precautions, drug interactions, and use in specific populations (see, e.g., 21 C.F.R. § 201.57 which is incorporated herein by reference in its entirety), and in some embodiments is required to be present on or associated with the drug for sale of the drug. Dosage forms comprising a sustained-release naltrexone formulation of the invention formulated in a compatible pharmaceutical carrier may also be prepared, placed in an appropriate container, and labeled for treatment of an indicated condition. In some embodiments, a kit is for sale of a prescription drug requiring the approval of and subject to the regulations of a governmental agency, such as the Food and Drug Administration of the United States. In some embodiments, the kit comprises the label or product insert required by the agency, such as the FDA, for sale of the kit to consumers, for example in the U.S.

The information may comprise instructions to administer the unit dosage form at a dosage of about 4 mg, about 8 mg, about 12 mg, about 16 mg, about 32 mg, or about 48 mg of naltrexone or a pharmaceutically acceptable salt thereof. The information may comprise instructions to administer the unit dosage form at a dosage of about 30 mg, about 90 mg, about 180 mg, about 360 mg, or about 4.50 mg of bupropion or a pharmaceutically acceptable salt thereof. These instructions may be provided in a variety of ways. The information may comprise instructions about when to administer the unit dosage forms. For example, the information may comprise instructions about when to administer the unit dosage forms relative to the administration of another medication or food, in preferred embodiments, the information instructs an individual to take naltrexone, or naltrexone and bupropion, with food, preferably a meal.

Some embodiments include information, preferably printed, that taking naltrexone or a pharmaceutically acceptable salt thereof with food results in an increase in the bioavailability of naltrexone or a pharmaceutically acceptable salt thereof compared to taking the same amount of naltrexone or a pharmaceutically acceptable salt thereof without food. Some embodiments include information, preferably printed, that taking bupropion or a pharmaceutically acceptable salt thereof with food results in an increase in the bioavailability of bupropion or a pharmaceutically acceptable salt thereof compared to taking the same amount of bupropion or a pharmaceutically acceptable salt thereof without food. Some embodiments include information, preferably printed, that taking naltrexone and bupropion, or a pharmaceutically acceptable salts thereof, with food results in an increase in the bioavailability of naltrexone and/or bupropion, or a pharmaceutically acceptable salts thereof, compared to taking the same amount of naltrexone and bupropion, or a pharmaceutically acceptable salts thereof, without food. Some embodiments include information, preferably printed, that taking naltrexone, and/or bupropion or pharmaceutically acceptable salts thereof with food results in fewer or less severe drug associated adverse events than taking the same amount of naltrexone and bupropion, or a pharmaceutically acceptable salts thereof, without food. In some embodiments, the adverse events are gastrointestinal events. In some embodiments, information regarding bioavailability, adverse events, or instructions on administration regimes are provided to a subject, a dosage form comprising the medication described in the information is provided to the subject, and the dosage form is administered in accordance to the information. In some embodiments the subject is a patient in need of the medication. In some embodiments the medication is administered as a therapy for a disease as described herein.

In some embodiments, the methods, compositions and kits disclosed herein may include information regarding enrolling and/or accessing a web-based and/or telephone-based weight management program. In some embodiments, the enrollment in a web-based and/or telephone-based weight management program is a requirement of obtaining the treatment medication. In some embodiments, the enrollment in a web-based and/or telephone-based weight management program is permitted only after obtaining a prescription for the treatment medication or the actual medication. In some embodiments, the method of treatment comprises enrolling in a web-based and/or telephone-based weight management program prior to and/or as a condition of receiving the treatment medication. In some embodiments, the information includes a unique login or enrollment key for enrolling and/or accessing a web-based and/or telephone-based weight management program.

Instructions and/or information may be present in a variety of forms, including printed information on a suitable medium or substrate (e.g., a piece or pieces of paper on which the information is printed), computer readable medium (e.g., diskette, CD, etc. on which the information has been recorded), or a website address that may be accessed via the internet. Printed information may, for example, be provided on a label associated with a drug product, on the container for a drug product, packaged with a drug product, or separately given to the patient apart from a drug product, or provided in manner that the patient can independently obtain the information (e.g., a website). Printed information may also be provided to a medical caregiver involved in treatment of the patient. In some embodiments, the information is provided to a person orally.

Some embodiments comprise a therapeutic package suitable for commercial sale. Some embodiments comprise a container. The container can be in any conventional shape or form as known in the art Which is made of a pharmaceutically acceptable material, for example a paper or cardboard box, a glass or plastic bottle or jar, a re-sealable bag (e.g., to hold a "refill" of tablets for placement into a different container), or a blister pack with individual dosages for pressing out of the pack according to a therapeutic schedule. The container employed can depend on the exact dosage form involved, e.g., a conventional cardboard box would not generally be used to hold a liquid suspension. It is feasible that more than one container can be used together in a single package to market a single dosage form. For example, tablets may be contained in a bottle which is in turn contained within a box. Non-limiting examples of packs and dispensers as well as oral dosage forms are disclosed in U.S.

Patent Publication Nos. 2008/0110792 and 2008/0113026, both of which are hereby incorporated herein by reference in their entirety and for all purposes, including without limitation for the purpose of describing combinations of naltrexone and bupropion, methods of making and formulating them into suitable dosage forms, methods of packing and dispensing them, and methods of administering them.

The information can be associated with the container, for example, by being: written on a label (e.g., the prescription label or a separate label) adhesively affixed to a bottle containing a dosage form described herein; included inside a container as a written package insert, such as inside a box which contains unit dose packets; applied directly to the container such as being printed on the wall of a box; or attached as by being tied or taped, e.g., as an instructional card affixed to the neck of a bottle via a string, cord or other line, lanyard or tether type device. The information may be printed directly on a unit dose pack or blister pack or blister card.

The term "bupropion" may be used in a general way herein to refer to a free base of bupropion, a pharmaceutically acceptable bupropion salt (including anhydrous forms, e.g., anhydrous bupropion), a bupropion metabolite (e.g., hydroxybupropion, threohydrobupropion, and erythrohydrobupropion), a bupropion isomer, or mixtures thereof.

The term "naltrexone" may be used in a general way herein to refer to a free base of naltrexone, a pharmaceutically acceptable naltrexone salt (including hydrates and anhydrous forms, e.g., naltrexone hydrochloride dihydrate and anhydrous naltrexone hydrochloride), a naltrexone metabolite, a naltrexone isomer, or mixtures thereof.

The term "pharmaceutically acceptable salt," as used herein, refers to a formulation of a compound that does not cause significant irritation to an organism to which it is administered and does not abrogate the biological activity and properties of the compound. Pharmaceutical salts can be obtained by routine experimentation Non-limiting examples of pharmaceutically acceptable salts include bupropion hydrochloride, radafaxine hydrochloride, naltrexone hydrochloride, and 6-βnaltrexol hydrochloride.

Throughout the present disclosure, when a particular compound is mentioned by name, for example, bupropion or naltrexone, it is understood that the scope of the present disclosure encompasses pharmaceutically acceptable salts, esters, amides, or metabolites of the named compound. For example, in any of the embodiments herein, an active metabolite of naltrexone (e.g., 6-βnaltrexol) can be used in combination with, or instead of, naltrexone. In any of the embodiments herein, an active metabolite of bupropion, including S,S-hydroxybupropion (i.e., radafaxine), can be used in combination with, or instead of, bupropion.

The term "sustained release," as used herein, has its ordinary meaning as understood by those skilled in the art and thus includes, by way of non-limiting example, the controlled release of a drug from a dosage form over an extended period of time. For example, in some embodiments, sustained-release dosage forms are those that have a release rate that is slower that of a comparable immediate release form, e.g., less than 80% of the release rate of an immediate-release dosage form.

An immediate-release naltrexone formulation appropriate for use as a reference standard is the immediate-release naltrexone formulation, widely available commercially as the REVIA® brand of naltrexone hydrochloride, or an equivalent thereof. An immediate-release bupropion formulation appropriate for use as a reference standard is the immediate-release bupropion formulation, widely available commercially as the WELLBUTRIN® brand of bupropion, or an equivalent thereof. The U.S. government regulates the manner in which prescription drugs can be labeled and thus reference herein to the REVIA® brand of naltrexone hydrochloride and WELLBUTRIN® brand of bupropion have well-known, fixed, and definite meanings to those skilled in the art.

The term "oral dosage form," as used herein, has its ordinary meaning as understood by those skilled in the art and thus includes, by way of non-limiting example, a formulation of a drug or drugs in a form administrable to a human, including pills, tablets, cores, capsules, caplets, loose powder, solutions, and suspensions.

The terms "mitigate" or "mitigation" of weight gain, as used herein, include preventing or decreasing the amount of weight gain associated, e.g., with the administration of a drug or a change in life activity. In some embodiments, mitigation of weight gain is measured relative to the amount of weight gain typically experienced when only one or neither of naltrexone or bupropion is administered.

The term "promotion" of weight loss, as used herein, includes causing weight loss relative to a baseline weight for a least a portion of the period of treatment. This includes an individual that initially gains some weight, but during the course of treatment loses weight relative to a baseline prior to beginning treatment, as well as individuals that regain a portion or all of the weight that is lost by the end of the treatment period. In a preferred embodiment, at the end of the treatment period, the individual has lost weight relative to a baseline. In a preferred embodiment, mitigation of weight gain or promotion of weight loss in a patient administered naltrexone and bupropion is greater than when neither or only one of naltrexone or bupropion is administered, and more preferably an at least additive, or better than additive, or synergistic, effect of administering the two compounds is achieved.

In any of the embodiments described herein, methods of treatment can alternatively entail use claims, such as Swiss-type use claims. For example, a method of treating overweight or obesity with a composition can alternatively entail the use of a composition in the manufacture of a medicament for the treatment of overweight or obesity, or the use of a composition for the treatment of overweight or obesity.

It is understood by those of skill in the art that numerous and various modifications can be made without departing from the spirit of the present invention. Therefore, it should be clearly understood that the embodiments of the present invention disclosed herein are illustrative only and are not intended to limit the scope of the present invention. Any reference referred to herein is incorporated by reference for the material discussed herein, and in its entirety.

EXAMPLES

The examples below are non-limiting and are merely representative of various aspects of the invention.

Example 1 summarizes the protocol for a clinical study demonstrating that treatment with Naltrexone SR/Bupropion SR does not increase or decreases the occurrence of Major Adverse Cardiovascular Events (MACE) in overweight and obese subjects with cardiovascular risk factors.

| |
|---|
| Example 1 |
| TITLE<br>A Multicenter, Randomized, Double-Blind, Placebo-Controlled Study Assessing the Occurrence of Major Adverse Cardiovascular Events (MACE) in Overweight and Obese Subjects With Cardiovascular Risk Factors Receiving Naltrexone SR/Bupropion SR |
| PRIMARY OBJECTIVE<br>• Demonstrate that 32 mg naltrexone sustained-release (SR)/360 mg bupropion SR (NB32) is no worse, or better compared to placebo on the occurrence of MACE, defined as cardiovascular death, nonfatal myocardial infarction, or nonfatal stroke in overweight and obese subjects. |
| SECONDARY OBJECTIVES<br>• Demonstrate NB32 is no worse or better compared to placebo on the occurrence of cardiovascular death, nonfatal myocardial infarction, nonfatal stroke, or nonfatal unstable angina requiring hospitalization in overweight and obese subjects.<br>• Demonstrate NB32 is no worse or better compared to placebo on the occurrence of each of the components of the primary objective in overweight and obese subjects. |
| OTHER OBJECTIVES<br>• Demonstrate that NB32 no worse or better than placebo on:<br>    ○ the occurrence of all cause mortality<br>    ○ the occurrence of unstable angina requiring hospitalization<br>    ○ the occurrence of coronary revascularization procedures<br>    ○ change in body weight<br>    ○ change in systolic and diastolic blood pressure |
| STUDY DESIGN<br>• This is a multicenter, randomized, double-blind, placebo-controlled study measuring the occurrence of MACE in overweight and obese subjects at increased risk of adverse cardiovascular outcomes receiving NB32.<br>• Approximately 9,880 subjects are enrolled into a double-blind lead-in period to identify subjects who do not tolerate treatment with low dose NB well or who exhibit other characteristics predictive of lack of compliance. At initiation of the lead-in period, subjects are randomly assigned in a 1:1 ratio to one of two treatment sequences: 1 week of active study medication (1 tablet per day) followed by 1 week of placebo (1 tablet per day), or 1 week of placebo followed by 1 week of active study medication. Eligible subjects are subsequently randomized to treatment with either NB32 or placebo in a 1:1 ratio. The duration of the randomized treatment period (or subject follow-up period for those who discontinue study medication early) is estimated to be between 2-4 years for most subjects.<br>• Subject enrollment may occur in two stages, with approximately 6,850 subjects enrolled to support accrual of sufficient events in randomized subjects for the interim analysis, and approximately 3,030 subjects subsequently enrolled to complete the study. Events in | randomized subjects from both stages of enrollment support the final analysis. Additional subjects may be recruited if withdrawal rates during the lead-in period are greater than anticipated.
- The study is conducted at approximately 300 centers.
- The study consists of three periods:

1) Screening Period (starting at Visit 1, Screen, with informed consent): up to 2 weeks to verify eligibility prior to the first dose of study medication in the lead-in period.

2) Lead-in Period (starting at Visit 2, Week -2): double-blind, 2-week period during which the subjects receive treatment according to one of two sequences: 1 week of active study medication (8 mg naltrexone SR/90 mg bupropion SR [NB]) once a day followed by 1 week of placebo once a day; or 1 week of placebo followed by 1 week of active study medication. Subjects are randomly assigned to NB or placebo for the lead-in period using a centralized Interactive Voice or Web Response System (IVRS/IWRS). Subjects are also required to record dietary intake information daily during this 2-week lead-in period. Regular use of food diaries (e.g., entries logged for a minimum of 10 out of 14 days) and study medication compliance (e.g., 10 out of 14 pills taken) is required for randomization to treatment. Subjects who discontinue study medication treatment or who had a suspected MACE event during the lead-in period are not eligible for randomization to treatment or participation in subsequent study procedures.

3) Treatment Period (starting at Visit 3, Day 1): double-blind, randomized period during which the subjects who completed the lead-in period and satisfied inclusion/exclusion criteria receive active study medication or placebo. The treatment period starts upon randomization at Visit 3 (Day 1). Randomized treatment assignment is via a centralized IVRS/IWRS. Each site is identified by a unique number, and each subject has a unique identifier assigned.

a) At Visit 6 (Week 16) there is an evaluation of weight loss and blood pressure changes relative to baseline observations. The target weight loss is $\geq 5\%$ with expected minimum weight loss at 16 weeks of $\geq 2\%$. Subjects should be discontinued from study medication at Week 16 if:
they have not lost at least 2% of their body weight *or*
they are experiencing sustained (e.g., at 2 or more visits) increases in blood pressure (systolic or diastolic) of $\geq 10$ mm Hg. If the Investigator suspects that an elevated blood pressure measurement may be spurious, subjects should not be discontinued until the elevated measurement is confirmed within 4 weeks.

b) All subjects participate in a comprehensive web-based weight management program as detailed above. Subjects participate in the weight management program through completion of study procedures, regardless of whether they are taking study medication.

c) Every other month between visits past Visit 7 (Week 26), subjects are asked to answer specific questions pertaining to compliance and hospitalizations (potential MACE or serious adverse events [SAEs]), using an internet- or telephone-based data collection system.

d) All randomized subjects who discontinue study medication early complete the End-of-Treatment Visit procedures and continue to participate in the study for the remainder of the trial for collection of MACE data. Subjects are asked to come to the study site at their scheduled visits and complete the internet- or telephone-based data collection every other month between visits past Visit 7 (Week 26) even though they are no longer taking study medication.

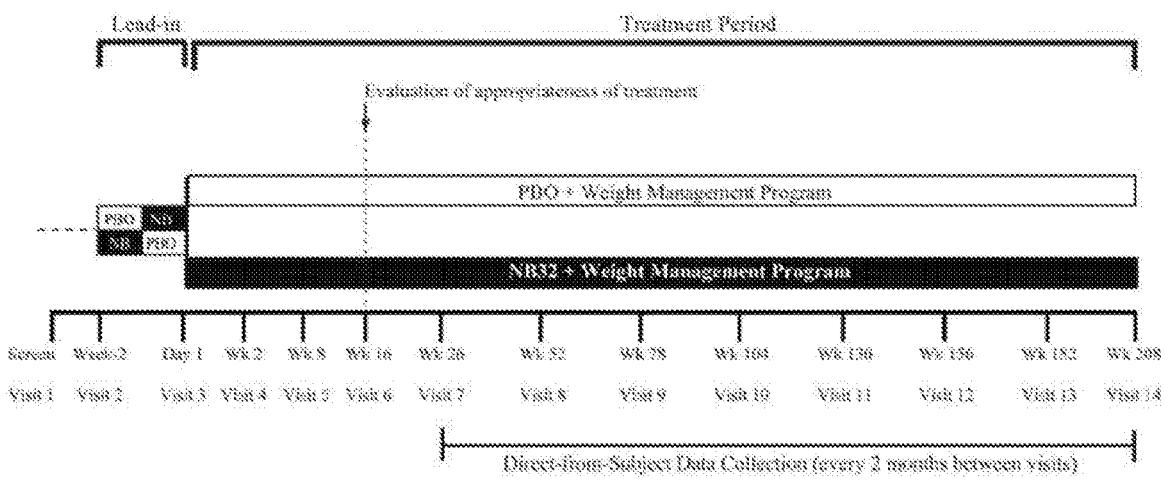

STUDY POPULATION
Overweight and obese subjects at increased risk of adverse cardiovascular outcomes are eligible to participate in this study. Approximately 9,880 subjects are enrolled into the double-blind lead-in period, and of those it is anticipated that 9,190 are randomized into the double-blind treatment period (i.e., approximately 7% of subjects are expected to discontinue the study during the lead-in period).

Inclusion Criteria
Subjects must meet all of the following inclusion criteria to be eligible for participation in this study.
1. ≥50 years of age (women) or ≥45 years of age (men)
2. Body mass index (BMI) ≥27 kg/m2 and ≤50 kg/m2
3. Waist circumference ≥88 cm (women) or ≥102 cm (men)
4. At increased risk of adverse cardiovascular outcomes:
   a. Cardiovascular disease (confirmed diagnosis or at high likelihood of cardiovascular disease) with at least one of the following:
      • History of documented myocardial infarction >3 months prior to screening
      • History of coronary revascularization (i.e., coronary artery bypass graft surgery, stent placement, percutaneous transluminal coronary angioplasty, or laser atherectomy)
      • History of carotid or peripheral revascularization (i.e., carotid endarterectomy, lower extremity atherosclerotic disease atherectomy, repair of abdominal aorta aneurysm, femoral or popliteal bypass)
      • Angina with ischemic changes (resting ECG), ECG changes on a graded exercise test (GXT), or positive cardiac imaging study
      • Ankle brachial index <0.9 (by simple palpation) within prior 2 years
      • ≥50% stenosis of a coronary, carotid, or lower extremity artery within prior 2 years
      and/or
   b. Type 2 diabetes mellitus with at least 2 of the following:
      • Hypertension (controlled with or without pharmacotherapy at <145/95 mm Hg)
      • Dyslipidemia requiring pharmacotherapy
      • Documented low HDL cholesterol (<50 mg/dL in women or <40 mg/dL in men) within prior 12 months
      • Current tobacco smoker.

Randomization of subjects with cardiovascular disease is targeted to be approximately 30% of all subjects randomized to study medication. Randomization of males with age ≥45 to <50 is targeted to be approximately 25% of all male subjects randomized to study medication, and randomization of females with age ≥50 to <55 is targeted to be approximately 25% of all female subjects randomized to study medication. The Data Monitoring Committee (DMC) may recommend adjusting these percentages, or other enrollment criteria, during the study conduct based on actual event rate observed and the overall distribution of the study population as it accrues.

Exclusion Criteria
1. Myocardial infarction within 3 months prior to screening
2. Angina pectoris Grade III or IV as per the Canadian Cardiovascular Society grading scheme (Table 3)
3. Clinical history of cerebrovascular disease (stroke)
4. History of tachyarrhythmia other than sinus tachycardia
5. Blood pressure ≥145/95 mm Hg, irrespective of treatment with antihypertensive agents
6. Unstable weight within 3 months prior to screening (e.g., weight gain or loss of >3%)
7. Planned bariatric surgery, cardiac surgery, or coronary angioplasty
8. Severe renal impairment defined by an estimated GFR <30 mL/min
9. Clinical history of liver failure or documented ALT or AST greater than 3 times the upper limit of normal (ULN)
10. Known infection with HIV or hepatitis
11. Chronic use or positive screen for opioids
12. Recent drug or alcohol abuse or dependence (with the exception of nicotine dependence) within 6 months prior to screening
13. History of seizures (including febrile seizures), cranial trauma, or other conditions that predispose the subject to seizures
14. History of mania or current diagnosis of active psychosis, active bulimia or anorexia nervosa (binge eating disorder is not exclusionary)
15. At risk for suicide attempts based on the judgment of the Investigator
16. Acute depressive illness including new onset of depression or acute exacerbation of symptoms (stable subjects on chronic treatment for depression are not excluded)
17. Any condition with life expectancy anticipated to be less than 4 years (e.g., congestive heart failure NYHA Class 3 or 4; Table 4)
18. History of malignancy within the previous 5 years, with exception of non-melanoma skin cancer or surgically cured cervical cancer
19. Current use of other bupropion or naltrexone containing products
20. History of hypersensitivity or intolerance to naltrexone or bupropion
21. Use of monoamine oxidase inhibitors within 14 days prior to screening
22. Use of any investigational drug, device, or procedure within 30 days prior to screening
23. Pregnant or breast-feeding women, or currently trying to become pregnant, or of child-bearing potential (including peri-menopausal women who have had a menstrual period within one year) and not willing to practice birth control
24. Inability to consistently access broadband internet
25. Employment by the Sponsor or the study site, or co-habitation with another individual enrolled in the study

STUDY MEDICATIONS
- The study medication (NB and placebo) is provided as tablets. Each active tablet contains 8 mg naltrexone SR/90 mg bupropion SR (8/90). All tablets, including placebo, are identical in appearance to maintain blinding. Dose escalation occurs during the first 4 weeks of the treatment period, as shown in the table below.
- Route of Administration: Oral. Doses can be taken with or without food.

| Dose Schedule | Lead-in Period | | Treatment Period | | | |
|---|---|---|---|---|---|---|
| | Week -2 | Week -1 | Week 1 (Days 1-7) | Week 2 (Days 8-14) | Week 3 (Days 15-21) | Week 4 through end of study |
| *Total Daily Dose** | *8/90 NB* | *8/90 NB* | *8/90 NB* | *16/180 NB* | *24/270 NB* | *32/360 NB* |
| Morning | 1 tab NB or PBO | 1 tab PBO or NB | 1 tab NB or PBO | 1 tab NB or PBO | 2 tabs NB or PBO | 2 tabs NB or PBO |
| Evening | -- | -- | -- | 1 tab NB or PBO | 1 tab NB or PBO | 2 tabs NB or PBO |

*Doses shown are of naltrexone SR/bupropion SR (NB); tab=tablet; PBO=placebo.

STUDY PROCEDURES
See Schedule of Study Procedures (Appendix 1).

ADVERSE EVENT COLLECTION
Potential cardiovascular events occurring during the lead-in and randomized treatment period of the study are collected and subjected to adjudication by an independent Clinical Endpoint Committee (CEC) to identify those events that meet the MACE endpoint definition. Deaths and potential cardiovascular events specified in this trial as endpoint events are exempted from the usual expedited regulatory reporting requirements, in keeping with 21 CFR 312.32(c)(5). All parties involved with the trial conduct at the site are to remain blinded to treatment assignment for subjects that have such events. Consistent with the well established general safety profile from both the NB phase 3 program and extensive clinical experience of both individual NB components, routine safety data collection is limited to adverse events leading to discontinuation of study medication and SAEs. Information on any in utero exposures and pregnancy outcomes are also collected. Safety data are reviewed on an ongoing basis by an independent DMC.

STATISTICAL ANALYSIS
Primary Endpoint:
- Time from treatment period randomization to the first confirmed occurrence of MACE, defined as cardiovascular death, nonfatal myocardial infarction, or nonfatal stroke.

Analysis Populations and Data Considerations:
- Enrolled: Subjects who take at least one dose of study medication during the lead-in period. Data from this population are not used in any formal statistical analyses.
- Intent-to-treat (ITT): Subjects who undergo randomization into the treatment period and are dispensed study medication. All post-randomization data in the treatment period are included in statistical analyses for this population. The ITT population is the primary analysis population for the primary endpoint and all secondary endpoints.
- Protocol: ITT subjects who take at least one dose of study medication in the treatment period in accordance with the study protocol. Data values observed up to and including 30 days after a subject's last confirmed treatment period dose date are included in all analyses for the Per Protocol population (referred to as on-treatment data), while data values outside of this window are excluded. The Per Protocol population is used for sensitivity analyses.

Hypotheses for the Primary Endpoint and Testing Procedure:
With respect to the primary endpoint, the following 3 null hypotheses are tested:
- H01: The hazard ratio for NB32 relative to placebo is $\geq 2.0$
- H02: The hazard ratio for NB32 relative to placebo is $\geq 1.4$
- H03: The hazard ratio for NB32 relative to placebo is $\geq 1.0$ (test for superiority)

In order to control the Type 1 error rate at the one-sided $\alpha=0.025$ level, a sequential testing procedure is used. The testing procedure is described below and is based on MACE confirmed by adjudication.
- Accrue at least 87 events.
- Conduct analysis to rule out a non-inferiority (NI) margin of 2.0 using all of alpha (testing H01).
- The trial must stop if the NI margin of 2.0 is not met. Note that when the true underlying hazard ratio is equal to 1, the least favorable hazard ratio point estimate that still results in non-inferiority for this test is 1.314.
- If the NI margin of 2.0 is met, all of alpha is recovered; the trial proceeds to at least 371 events to rule out the NI margin of 1.4 at the end of the study (testing H02).
- The final analysis to rule out the NI margin of 1.4 is conducted using all of alpha without adjustment since it is the first analysis against the NI margin of 1.4. The first analysis with 87 events is not used to rule out the NI margin of 1.4 and hence no multiplicity control is needed between this analysis and the analyses against the NI margin of 2.0. Note that when the true underlying hazard ratio is equal to 1, the least favorable hazard ratio point estimate that will still result in non-inferiority for this test is 1.142.
- If H02 is successfully rejected, the analysis proceeds to test H03 using all of alpha. This is the gated test for superiority.

Choice of NI Margin:
In a study population with an annual background MACE rate of 1.0-1.5%:
- The pre-approval NI margin of 2.0 corresponds to ruling out an excess of 10-15 additional events per 1,000 subject-years with an absolute risk difference of 1.0-1.5%.
- The post-approval NI margin of 1.4 corresponds to ruling out an excess of 4-6 additional events per 1,000 subject-years with an absolute risk difference of 0.4-0.6%.

Secondary Endpoints:
- Time from treatment period randomization to the first confirmed occurrence of cardiovascular death, nonfatal myocardial infarction, nonfatal stroke, or nonfatal unstable angina requiring hospitalization
- Time from treatment period randomization to the confirmed occurrence of cardiovascular death (including fatal myocardial infarction, fatal stroke)
- Time from treatment period randomization to the first confirmed occurrence of myocardial infarction (nonfatal or fatal)
- Time from treatment period randomization to the first confirmed occurrence of stroke (nonfatal or fatal)

Other Endpoints:
- Time from treatment period randomization to the confirmed occurrence of death from any cause
- Time from treatment period randomization to the first confirmed occurrence of unstable angina requiring hospitalization (nonfatal or fatal)
- Time from treatment period randomization to the first occurrence of coronary revascularization procedure
- Percent change in body weight from baseline to Week 52
- Proportion of subjects achieving ≥10% body weight reduction from baseline at Week 52
- Change in blood pressure from baseline to Week 52

Sample Size:
The following assumptions were used to determine the number of confirmed MACE required for the final analysis against a NI margin of 1.4 for the primary hypothesis in the primary analysis population (ITT).
- Underlying hazard ratio of active to control: 1
- NI margin: 1.4
- One-sided $\alpha = 0.025$
- At least 90% power at the final analysis to establish that the upper bound of a one-sided 97.5% confidence interval for the hazard ratio will fall below the pre-specified NI margin.

Under these assumptions, the trial requires 371 events. Similarly, 87 events provides 90% power for the NI margin of 2.0.
To estimate sample size for the ITT population, the following assumptions are used in addition to those listed above. These assumptions are necessary to allow a sample size to be calculated.

However, since this is an event-driven study, the power for the study is based on the number of MACE rather than the number of subjects. The assumptions used below represent a single cohort of subjects randomized in one stage for the final analysis and do not incorporate potential variations such as enrollment of subjects in more than one stage. Accordingly, the actual sample size may vary from the sample size calculation provided in this protocol depending on the actual accrual of events.

- Recruitment period: 1.5 years
- 1:1 randomization
- Maximum subject follow-up: 4 years
- Lost to follow up (LTFU) rate: 0.012 annual LTFU
- Primary MACE endpoint annualized event rate: 1.5% in the control group Under these assumptions, the trial requires N=3,955 subjects per treatment group. However, the number of subjects planned is N=4,593 per treatment group to allow for accrual of a sufficient number of events in case of minor departures from event rate, recruitment and retention rates, and underlying hazard ratio assumptions.

This event-driven study is stopped when at least 371 MACE have been confirmed. Accrual of 371 confirmed MACE provides 90% power for the primary analysis with a NI margin of 1.4 in the ITT population (H02). The least favorable hazard ratio that can still result in a non-inferiority result for H02 is 1.142 when the true underlying hazard ratio is equal to 1. With this number of events and the expected discontinuation rate from study medication, there are a sufficient number of confirmed on-treatment MACE to provide high probability that the hazard ratio estimate in the Per Protocol population is less than 1.142 assuming the true underlying hazard ratio is equal to 1. Similarly, in the analysis using a NI margin of 2.0, accrual of at least 87 confirmed MACE provides 90% power in the ITT population with the least favorable hazard ratio that can still result in a non-inferiority result for H01 being 1.314 when the true underlying hazard ratio is equal to 1. There are a sufficient number of confirmed on-treatment MACE to provide high probability that the hazard ratio estimate in the Per Protocol population is less than 1.314 assuming the true underlying hazard ratio is equal to 1.

| APPENDIX 1: SCHEDULE OF STUDY PROCEDURES | | | | | | | | | | |
|---|---|---|---|---|---|---|---|---|---|---|
| Period: | Screening | Lead-in | Treatment | | | | | | | |
| | Visit 1 (Screening) | Visit 2 (Wk -2) | Visit 3 (Day 1) (Baseline) | Visit 4 (Wk 2) | Visit 5 (Wk 8) | Visit 6 (Wk 16) | Visit 7-13 (Wks 26, 52, 78, 104, 130, 156, 182) | Visit 14 (Wk 208; End-of-Study)[5] | End of Treatment Visit[6] | Remote Contacts[7] |
| Informed Consent | X | | | | | | | | | |
| Eligibility Criteria | X | X | X (labs) | | | | | | | |
| Demographics | X | | | | | | | | | |
| Medical History | X | | | | | | | | | |
| Height | X | | | | | | | | | |
| Weight | X | X | X | X | X | X | X | X | X | |
| Waist Circumference | X | | | | | | | X | X | |
| Vital Signs (BP and HR) | X | X | X | X | X | X | X | X | X | |
| Concomitant Medications | X | | | | | | X[1] | X | X | |
| Pregnancy Test (urine)[2] | | X | | | | | | | | |
| Drug Screen (urine) | | X | | | | | | | | |
| Chemistry, Hematology, Urinalysis, Lipids, HbA1c, hsCRP | | X | | | | | | | | |
| Electrocardiogram | | X | | | | | | | | |
| Enrollment and Lead-in Randomization | | X | | | | | | | | |
| Study Training | | X | X | | | | X[3] | | | |
| Evaluation of Study Medication and | | | X | | | | | | | |
| Food Diary Compliance | | | X | | | | | | | |
| Treatment Randomization | | | X | | | | | | | |
| MACE | | | X | X | X | X | X | X | X | X |
| SAEs, AEs Leading to Discontinuation, Pregnancies | | | X | X | X | X | X | X | X | X |
| Weight Management Program | | | ⟶ | | | | | | | |
| Evaluation to Continue Treatment | | | | | | X | | | | |
| Study Medication Dispensing/Return[4] | | X | X | | X | X | X | X | X | |
| Study Medication Compliance | | | X | X | X | X | X | X | X | X |

The visit window for Visit 3 (Day1) is ±3 days relative to Visit 2 (Week -2). Post-baseline visit windows are ±3 days at Visit 4, ±1 week at Visit 5 and 6, ±2 weeks for subsequent visits.
[1]For Visits 8, 10, and 12 only.
[2]Women of child-bearing potential (including peri-menopausal women who have had a menstrual period within one year) only.
[3]Visit 7 training will focus on remote internet or telephone contact procedures.
[4]Visit 2 = dispensing only, Visit 14/End-of-Study Visit, and End-of-Treatment Visit = return only.
[5]Subjects with an End-of-Treatment Visit will not return study medication or have compliance or concomitant medications recorded at Visit 14/ End-of-Study Visit.
[6]Subjects who discontinue study medication before Week 208 will be asked to return to the study site for the indicated end-of-treatment assessments, and asked to return for their remaining visits through Week 208 for follow-up.
[7]After Visit 7 and through the remainder of the study, subjects will answer specific questions pertaining to compliance and any occurrence of hospitalization through an internet or telephone based data collection system every 2 months between visits. Hospitalization information will be used to identify potential MACE or SAEs.

| |
|---|
| Example 2 |
| TITLE<br>A Multicenter, Randomized, Open-Label, Controlled, Method-of-Use Study Assessing the Effect of Naltrexone SR/Bupropion SR on Body Weight and Cardiovascular Risk Factors in Overweight and Obese Subjects |
| PRIMARY OBJECTIVE<ul><li>To assess the effect of the intended clinical method of use of 32 mg naltrexone sustained release (SR)/360 mg bupropion SR (NB) in conjunction with a comprehensive lifestyle intervention (CLI) program compared to Usual Care (minimal lifestyle intervention program) on body weight at Week 26 in subjects who are overweight with dyslipidemia and/or controlled hypertension or obese</li></ul> |
| SECONDARY OBJECTIVES<ul><li>To assess the effect of NB and CLI compared to Usual Care on:<ul><li>The percentage of subjects achieving a loss of at least 5%, 10%, and 15% of baseline body weight at Week 26</li><li>Changes in cardiovascular risk factors (waist circumference and lipids) at Week 26</li><li>Changes in vital signs (systolic and diastolic blood pressure and heart rate) at Week 26</li><li>Changes in measures of glucose metabolism (fasting glucose, insulin, and homeostasis model assessment – insulin resistance [HOMA-IR]) at Week 26</li><li>Changes in patient reported measures of eating behavior (Binge Eating Scale [BES]), sexual function (Arizona Sexual Experiences [ASEX] Scale), and weight-related quality of life (Impact of Weight on Quality of Life-Lite Questionnaire [IWQOL-Lite]) at Week 26.</li></ul></li></ul> |
| ADDITIONAL OBJECTIVES<br><ul><li>To assess the effect of NB and CLI compared to Usual Care on change in body weight from baseline to post-baseline visits through Week 20</li><li>To assess the effect of NB and CLI compared to Usual Care on changes in patient reported measures of eating behavior, sexual function, and weight-related quality of life at Week 16</li><li>To assess the longer term effects of NB and CLI (beyond 26 weeks) on body weight, cardiovascular risk factors, vital signs, and glucose metabolism</li></ul> |
| STUDY DESIGN<ul><li>This is a Phase 3b, multicenter, randomized, open-label, controlled study to assess the effects of NB, used in a manner consistent with its intended use after marketing approval, on body weight and cardiovascular risk factors compared to the effects of Usual Care in subjects who are overweight with dyslipidemia and/or controlled hypertension or obese.</li><li>A minimum of 198 and up to 242 subjects will be randomly assigned to either NB or Usual Care in a 1.75:1 ratio across approximately 15 centers in the United States. Subjects randomized to receive NB will also participate in an internet-based CLI program that includes a progressive nutrition and exercise program with goal setting and tracking tools. Subjects randomized to receive Usual Care will participate in a minimal lifestyle intervention program consisting of periodic education/advice from study site personnel. After 26 weeks, all subjects will receive NB and CLI through Week 78.</li></ul><ul><li>The study consists of three periods:</li></ul>1) Screening Period (starting at Visit 1): up to 2 weeks to verify eligibility prior to randomization.<br>2) Controlled Treatment Period ((Visit 2 [Day 1] to Visit 8 [Week 26]): open-label period | during which subjects who satisfied inclusion/exclusion criteria will receive active study medication (NB) and CLI or Usual Care (no study medication and minimal lifestyle intervention program). Subjects will be randomly assigned to their treatment group using a centralized Interactive Voice or Web Response System (IVRS/IWRS).
   a) Subjects in either treatment group who discontinue from full participation will not continue with scheduled study procedures but will be instructed to return to the study site at Weeks 26, 52, and 78 to have their weight measured. Subjects randomized to NB who discontinue from full participation will also discontinue study medication but will be allowed to continue participation in the CLI program for the remainder of the study.
   b) At Visit 6 (Week 16) there will be an evaluation of weight loss and blood pressure changes relative to baseline observations for subjects randomized to NB. NB-treated subjects should be discontinued from full participation at Week 16 if:
      ○ they have not lost at least 5% of their baseline body weight *or*
      ○ they are experiencing sustained (i.e., at Visit 5 [Week 10] and Visit 6 [Week 16]) increases in blood pressure (systolic or diastolic) of ≥10 mm Hg 3) Uncontrolled Treatment Period (Visit 8 [Week 26] to Visit 15 [Week 78]): open-label treatment period.
   a) Subjects originally randomized to and still taking NB as directed will continue their study medication and continue to participate in the CLI program.
   b) Subjects originally randomized to Usual Care will switch to NB, in conjunction with CLI at Week 26. Subjects who switch to NB and CLI will follow the same NB dosing schedule, CLI curriculum, and evaluation of weight loss and blood pressure changes for continuing with therapy as subjects originally randomized to NB and CLI, only 26 weeks later in the study.
   c) Subjects who discontinue from full participation will not continue with scheduled study procedures but will be instructed to return to the study site at Weeks 52 (if applicable) and 78 to have their weight measured. Subjects who discontinue from full participation will also discontinue study medication but will be allowed to continue participation in the CLI program for the remainder of the study.

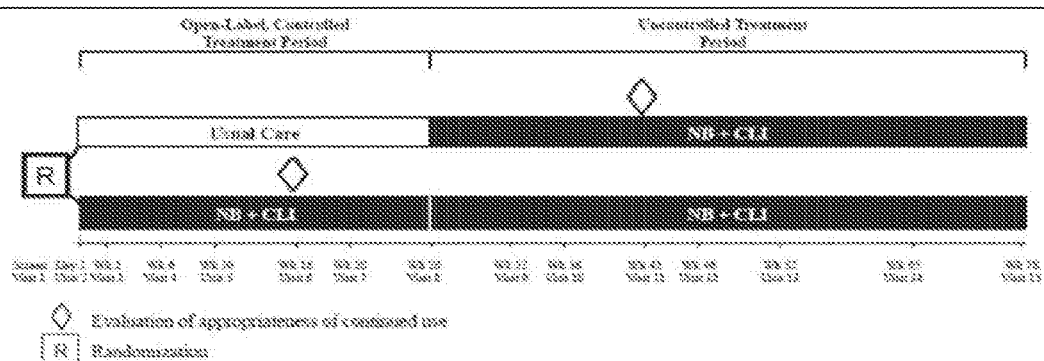

◇ Evaluation of appropriateness of continued use
R Randomization

STUDY POPULATION
A minimum of 198 and up to 242 overweight or obese subjects who are eligible to participate will be randomized into the study.

Inclusion Criteria
Subjects must meet all of the following inclusion criteria to be eligible for participation in this study.
1. Female or male subjects, 18 to 60 years, inclusive, of age
2. Body mass index (BMI) ≥30 and ≤45 kg/m2 for subjects with uncomplicated obesity, and BMI of ≥27 and ≤45 kg/m2 for subjects who are overweight or obese and have dyslipidemia and/or controlled hypertension

Exclusion Criteria

Subjects meeting any of the following exclusion criteria will not be eligible for participation in this study.
1. History of type 1 or type 2 diabetes mellitus diagnosis
2. Myocardial infarction within 6 months prior to screening (Visit 1)
3. Angina pectoris Grade III or IV as per the Canadian Cardiovascular Society grading scheme (Table 3)
4. Clinical history of large vessel cortical strokes, including ischemic and hemorrhagic strokes (i.e., transient ischemic attack is not exclusionary)
5. Blood pressure ≥145/95 mm Hg at screening (Visit 1) or randomization (Visit 2)
6. Initiation or alteration of dose of lipid-lowering agents within 4 weeks prior to screening (Visit 1)
7. History (within the last 20 years) of seizures, cranial trauma, bulimia, anorexia nervosa, or other conditions hat predispose the subject to seizures
8. Unstable weight (i.e., weight gain or loss of >3%) within 3 months prior to screening (Visit 1)
9. Use of prescribed or over-the-counter drugs intended for weight loss, or participation in a weight loss program within one month prior to screening (Visit 1)
10. Planned surgical or device intervention for obesity (e.g., gastric banding)
11. Current or history of severe renal impairment, defined by an estimated glomerular filtration rate (GFR) <30 mL/min/1.73 m$^2$
12. Clinical history of liver failure or current documented aspartate aminotransferase (AST) or alanine aminotransferase (ALT) >3 times the upper limit of normal (ULN) at screening (Visit 1)
13. Fasting glucose ≥126 mg/dL or fasting triglycerides ≥400 mg/dL at screening (Visit 1)
14. Current known infection with HIV or hepatitis (documentation of no detectable virus is required for subjects with a past infection of hepatitis B or C)
15. Chronic use or positive screen for opioids at screening (Visit 1)
16. Drug or alcohol abuse or dependence within 6 months prior to screening (Visit 1) or positive urine drug screen
17. Regular use of tobacco products (an average of at least 1 product per day) including inhaled tobacco (such as cigarettes, cigars, pipes, etc.), chewing tobacco or snuff, or nicotine replacement products in the 6 months prior to screening (Visit 1)
18. History of mania or current diagnosis of active psychosis
19. At risk for suicide attempts based on the judgment of the Investigator
20. Acute depressive illness, including new onset of depression or acute exacerbation of symptoms (stable subjects on chronic treatment for depression are not excluded)
21. Current use of other bupropion- or naltrexone-containing products or a history of hypersensitivity or intolerance to naltrexone or bupropion
22. Current use of anticonvulsant agents, dopamine agonists, theophylline, or oral corticosteroids or use of monoamine oxidase inhibitors within 14 days prior to screening (Visit 1)
23. Use of any investigational drug, device, or procedure within 30 days prior to screening (Visit 1)
24. Pregnant or trying to become pregnant, currently breast-feeding, or of child-bearing potential (including perimenopausal women who have had a menstrual period within one year) and not willing to practice birth control using a double barrier method (criteria apply to women only)
25. Any clinically significant electrocardiogram, laboratory, hematology, physical exam, medical history, or urinalysis finding that in the investigator's opinion should prohibit participation in the study
26. Inability or unwillingness to perform regular, moderate-intensity exercise, such as brisk walking
27. Inability to access broadband internet or email daily (analog or dial-up access is not acceptable)
28. Inability to complete a test of email use and CLI program access prior to randomization (Visit 2)
29. Inability to comply with all required study procedures and schedule, inability to speak and read English, or unwillingness or inability to give written informed consent
30. Employee or immediate family member of the Sponsor or member of the study site research staff, or cohabitation with another individual randomized in the study

STUDY MEDICATIONS
- The study medication (NB) will be provided as tablets. Each tablet will contain 8 mg naltrexone SR/90 mg bupropion SR. Dose escalation will occur during the first 4 weeks of the Controlled Treatment Period for subjects initially randomized to NB and during the first 4 weeks of the Uncontrolled Treatment Period for subjects initially randomized to the Usual Care group, as shown in the table below.
- Route of Administration: Oral. Doses can be taken with or without food. Tablets must be swallowed whole, and should not be cut or crushed.

| NB Dose Schedule | 1st Week | 2nd Week | 3rd Week | 4th Week to study end |
|---|---|---|---|---|
| Morning | 1 NB tablet | 1 NB tablet | 2 NB tablets | 2 NB tablets |
| Evening | -- | 1 NB tablet | 1 NB tablet | 2 NB tablets |
| *Total Naltrexone/Bupropion Daily Dose (mg)* | *8/90* | *16/180* | *24/270* | *32/360* |

Subjects in both treatment groups will follow the same NB dose schedule but at different points in the study. Subjects randomized to NB will initiate NB treatment at Week 1; subjects randomized to Usual Care will initiate NB treatment at Week 26.

STUDY PROCEDURES
See Schedule of Study Procedures (Appendix 2).

STATISTICAL ANALYSIS

Analysis Population Definitions:
- Randomized: Subjects who undergo randomization into the Controlled Treatment Period.
- Intent-to-Treat (ITT): Subjects randomized to NB and CLI who have received at least one dose of study medication and subjects randomized to Usual Care who have received their baseline lifestyle intervention program instruction.
- Modified ITT (mITT): Subjects from the ITT population who have completed the Week 2 study visit, have a baseline body weight measurement, and have at least one postbaseline body weight measurement. Subjects randomized to the NB and CLI group must still be taking study medication at the Week 2 study visit.
- Week 26 Per Protocol (PP): Subjects from the ITT population who have completed the study through Week 26 in compliance with the protocol. Subjects randomized to the NB and CLI group must have passed the evaluation of weight loss and blood pressure changes for continuing with therapy at Week 16 and still be taking study medication at the Week 26 study visit.
- Week 52 Per Protocol (PP): Subjects from the Week 26 PP population who have completed the study through Week 52 (on study medication at Week 52) and in compliance with the protocol. Subjects who switched from Usual Care to NB and CLI must have passed the evaluation of weight loss and blood pressure changes for continuing with therapy at Week 42.
- Week 78 Per Protocol (PP): Subjects from the Week 52 PP population who have completed the study through Week 78 (on study medication at Week 78) and in compliance with the protocol.

The primary efficacy and safety analysis populations are the Week 26 PP and ITT populations, respectively.

Primary Study Endpoint:
- Percent change in body weight from baseline (Day 1) to Week 26.

Secondary Study Endpoints
- Percentage of subjects achieving a loss of at least 5%, 10%, and 15% of baseline body weight at Week 26
- Absolute change in body weight from baseline to Week 26
- Changes in cardiovascular risk factors from baseline to Week 26, including:
  - Waist circumference
  - Fasting triglycerides
  - Fasting LDL cholesterol
  - Fasting HDL cholesterol
- Changes in vital signs from baseline to Week 26, including:
  - Systolic and diastolic blood pressure
  - Heart rate
- Changes in measures of glucose metabolism from baseline to Week 26, including:
  - Fasting glucose
  - Fasting insulin
  - HOMA-IR
- Changes in measurements derived from patient reported outcomes from baseline to Week 26, including:
  - Eating behavior (BES)
  - Sexual function (ASEX Scale)
  - Weight-related quality of life (IWQOL-Lite)

Additional Study Endpoints
- Changes in body weight, cardiovascular risk factors, vital signs, glucose metabolism, and patient reported outcomes from baseline to post-baseline visits (prior to and after Week 26, as applicable)
- Changes in body weight, cardiovascular risk factors, vital signs, and glucose metabolism from baseline of Uncontrolled Treatment Period (Week 26) to post-Week 26 visits (in particular, the Week 52 and Week 78 visits).

Sample Size
The sample size was calculated by estimating the number of subjects required to have ≥90% power to detect a significant difference ($\alpha=0.05$) between the treatment groups at Week 26 for the Week 26 PP Population using a two-sample t-test with the following assumptions:
- Effect size between 0.6 and 0.75, which is within the range observed in the NB Phase 3 clinical program
- Overall discontinuation rate from full participation between randomization and Week 26: 60% for NB and CLI (includes discontinuation due to the Week 16 assessment) and 30% for Usual Care
- A 1.75:1 randomization to account for the assumed differential rate of discontinuation from full participation for the treatment groups at Week 26
- Two-sided $\alpha=0.05$ Under these assumptions, between 198 and 242 randomized subjects are required to detect a significant difference between groups for the approximately 80 to 120 subjects (39 to 60 per treatment group) expected to comprise the Week 26 PP population. The assumptions for effect size and discontinuation rates from full participation are based on data from the NB Phase 3 clinical program and scientific publications pertaining to usual care for obesity (*See*, Wadden, et al., "A two-year randomized trial of obesity treatment in primary care practice," N Engl J. Med. 2011, 365(21):1969-1979; Tsai, et al., "A primary care intervention for weight loss: results of a randomized controlled pilot study," Obesity, 2010, 18(8): 1614-1618), herein incorporated by reference in its entirety.

Appendix 2: Schedule of Study Procedures for Example 2

|  | Screening | Controlled Treatment Period | | | | | | |
|---|---|---|---|---|---|---|---|---|
|  | Visit 1 (Screen)[1] | Visit 2 (Day 1) (Baseline)[1] | Visit 3 (Wk 2)[1] | Visit 4 (Wk 6) | Visit 5 (Wk 10) | Visit 6 (Wk 16)[1] | Visit 7 (Wk 20) | Visit 8 (Wk 26)[1] |
| Informed Consent | X | | | | | | | |
| Eligibility Criteria | X | X | | | | | | |
| Demographics | X | | | | | | | |
| Medical History | X | X | | | | | | |
| Height | X | | | | | | | |
| Electrocardiogram, Physical Exam | X | | | | | | | |
| Chemistry, Hematology, Urinalysis, Drug Screen (urine) | X | | | | | | | |
| Randomization | | X | | | | | | |
| Weight, Vital Signs (BP, HR) | X | X | X | X | X | X | X | X |
| Waist Circumference | | X | | | | X | | X |
| Concomitant Medication Review | X | X | X | X | X | X | X | X |
| Pregnancy Test (urine)[2] | X | X | X | X | X | X | X | X |
| Lipids, Glucose, Insulin[3] | X (glucose, TGs only) | X | | | | X | | X |
| Patient Reported Outcome Measures (BES, ASEX, IWQOL-Lite) | | X | | | | X | | X |
| Query for SAEs | | | X | X | X | X | X | X |
| Minimal Lifestyle Intervention (Usual Care only) | | X | | | X | | | |
| Evaluation to Continue Treatment (NB only) | | | | | | X | | |
| Review CLI participation (NB only) | | X | X | X | X | X | X | X[5] |
| Study Medication Dispensing/Return (NB only) | | X[6] | | X | X | X | X | X[7] |
| Study Medication Compliance (NB only) | | | X | X | X | X | X | X |

The visit window between Visit 1 (Screening) and Visit 2 (Day 1: Baseline) is up to 2 weeks. Visit windows are ±3 days at Visit 3 and 4; ±1 week at Visits 5,6,7, and 8 relative to Visit 2.

[1] Subjects should arrive having fasted (no food or beverage except water) overnight for at least 8 hours before this visit. Subjects should receive a call from a member of the study site staff 1 to 3 days prior to these visits (except Visit 1) reminding them to fast for at least 8 hours prior to the visit.
[2] Women of child bearing potential (including peri-menopausal women who have had a menstrual period within one year) only.
[3] Glucose and triglycerides at Visit 1 are to confirm subject eligibility. Measures at Visit 2 are to obtain baseline values.
[4] Subjects are to be registered for the CLi program and reveice instruction at this visit.
[5] Subjects randomized to Usual Care who switch to NB and CLI are to be registered for the CLI program and receive instructions ar this visit.
[6] Dispensing only at this visit.
[7] Subjects randomized to Usual Care who switch to NB and CLI are to be dispensed study medication at this visit.

|  | Uncontrolled Treatment Period | | | | | | | End of Full Participation Visit |
|---|---|---|---|---|---|---|---|---|
|  | Visit 9 (Wk 12) | Visit 10 (Wk 36) | Visit 11 (Wk 42)* | Visit 12 (Wk 48) | Visit 13 (Wk 52)* | Visit 14 (Wk 60) | Visit 15 (Wk 78)* |  |
| Weight, Vital Signs (BP, HR) | X | X | X | X | X | X | X | X |
| Waist Circumference |  |  | X |  | X |  | X | X |
| Concomitant Medication Review |  |  |  |  | X |  | X | X |
| Pregnancy Test (urine) | X | X | X | X | X | X | X | X |
| Lipids, Glucose, Insulin |  |  | X |  | X |  | X |  |
| Patient Reported Outcome Measures (BES, ASEX, IWQOL-Lite) |  |  |  |  |  |  |  | X[c] |
| Query for SAEs | X | X | X | X | X | X | X | X |
| Evaluation to Continue Treatment (Usual care → NB only) |  |  | X |  |  |  |  |  |
| Review CLI participation | X | X | X | X | X | X | X | X[c] |
| Study Medication Dispensing/Return | X | X | X | X | X | X | X[d] | X[d] |
| Study Medication Compliance | X | X | X | X | X | X | X | X |

Table 3: Canadian Cardiovascular Society grading scheme for angina pectoris

| Grade | Description |
|---|---|
| Grade I | Ordinary physical activity does not cause angina, such as walking and climbing stairs. Angina with strenuous or rapid or prolonged exertion at work or recreation. |
| Grade II | Slight limitation of ordinary activity. Walking or climbing stairs rapidly, walking uphill, walking or stair climbing after meals, or in cold, or in wind, or under emotional stress, or only during the few hours after awakening. Walking more than two blocks on the level and climbing more than one flight of ordinary stairs at a normal pace and in normal conditions. |
| Grade III | Marked limitation of ordinary physical activity. Walking one or two blocks on the level and climbing one flight of stairs in normal conditions and at normal pace. |
| Grade IV | Inability to carry on any physical activity without discomfort, angina syndrome may be present at rest. |
| Campeau, 1976. Available on the Canadian Cardiovascular Society Website at www.ccs.ca | |

TABLE 3

Canadian Cardiovascular Society grading scheme for angina pectoris

| Grade | Description |
|---|---|
| Grade I | Ordinary physical activity does not cause angina, such as walking and climbing stairs. Angina with strenuous or rapid or prolonged exertion at work or recreation. |
| Grade II | Slight limitation of ordinary activity. Walking or climbing stairs rapidly, walking uphill, walking or stair climbing after meals, or in cold, or in wind, or under emotional stress, or only during the few hours after awakening. Walking more than two blocks on the level and climbing more than one flight of ordinary stairs at a normal pace and in normal conditions. |
| Grade III | Marked limitation of ordinary physical activity. Walking one or two blocks on the level and climbing one flight of stairs in normal conditions and at normal pace. |
| Grade IV | Inability to carry on any physical activity without discomfort, angina syndrome may be present at rest. |

Campeau, 1976. Available on the Canadian Cardiovascular Society Website at www.ccs.ca

TABLE 4

New York Heart Association: the stages of heart failure

| Class | Patient symptoms |
|---|---|
| Class I (Mild) | No limitation of physical activity. Ordinary physical activity does not cause undue fatigue, palpitation, or dyspnea (shortness of breath). |
| Class II (Mild) | Slight limitation of physical activity. Comfortable at rest, but ordinary physical activity results in fatigue, palpitation, or dyspnea. |
| Class III (Moderate) | Marked limitation of physical activity. Comfortable at rest, but less than ordinary activity causes fatigue, palpitation, or dyspnea. |
| Class IV (Severe) | Unable to carry out any physical activity without discomfort. Symptoms of cardiac insufficiency at rest. If any physical activity is undertaken, discomfort is increased. |

Available on the Heart Failure Society of America website at www.abouthf.org

What is claimed is:

1. A method of treating overweight or obesity in a subject at increased risk of a major adverse cardiovascular event, the method comprising:
   administering to an overweight or obese subject at increased risk of a major adverse cardiovascular event an amount of sustained release naltrexone or a pharmaceutically acceptable salt thereof in a range of about 4 mg to about 50 mg per day and an amount of sustained release bupropion or a pharmaceutically acceptable salt thereof in a range of about 30 mg to about 500 mg per day;
   wherein said overweight or obese subject is at increased risk of a major adverse cardiovascular event if said subject has been diagnosed as having cardiovascular disease with at least one risk factor selected from the group consisting of:
   a history of documented myocardial infarction >3 months prior to said identification;
   a history of coronary revascularization including coronary artery bypass graft surgery, stent placement, percutaneous transluminal coronary angioplasty, or laser atherectomy;
   angina with ischemic changes, ECG changes on a graded exercise test, or positive cardiac imaging study;
   ankle brachial index <0.9 assessed by simple palpation within prior 2 years of said identification; and
   >50% stenosis of a coronary, carotid, or lower extremity artery within prior 2 years of said identification; and
   wherein said subject is treated for at least 16 weeks.

2. The method of claim 1, wherein said subject does not have Type 2 diabetes mellitus with at least 2 risk factors selected from the group consisting of:
   hypertension controlled with or without pharmacotherapy at <145/95 mm Hg; dyslipidemia requiring pharmacotherapy;
   documented low HDL cholesterol, <50 mg/dL in women or <40 mg/dL in men, within prior 12 months of said identification; and
   current tobacco smoker.

3. The method of claim 1, wherein the subject achieves a percentage of weight loss of at least 5%.

4. The method of claim 1, wherein administering the naltrexone and bupropion does not increase said subject's risk of an adverse cardiovascular outcome.

5. The method of claim 1, wherein said adverse cardiovascular outcome is cardiovascular death, nonfatal myocardial infarction, or nonfatal stroke.

6. The method of claim 1, wherein the subject is administered said sustained release naltrexone, or a pharmaceutically acceptable salt thereof, and said sustained release bupropion, or a pharmaceutically acceptable salt thereof, in a tablet containing 8 mg of sustained release naltrexone and 90 mg of sustained release bupropion.

7. A method of treating overweight or obesity in a subject at increased risk of a major adverse cardiovascular event, the method comprising:
   administering to an overweight or obese subject at increased risk of a major adverse cardiovascular event an amount of sustained release naltrexone or a pharmaceutically acceptable salt thereof in a range of about 4 mg to about 50 mg per day and an amount of sustained release bupropion or a pharmaceutically acceptable salt thereof in a range of about 30 mg to about 500 mg per day;

wherein said overweight or obese subject is at increased risk of a major adverse cardiovascular event if said subject has been diagnosed as having cardiovascular disease with at least one risk factor selected from the group consisting of:
- a history of documented myocardial infarction >3 months prior to said identification;
- a history of coronary revascularization including coronary artery bypass graft surgery, stent placement, percutaneous transluminal coronary angioplasty, or laser atherectomy;
- angina with ischemic changes, ECG changes on a graded exercise test, or positive cardiac imaging study;
- ankle brachial index <0.9 assessed by simple palpation within prior 2 years of said identification; and
- ≥50% stenosis of a coronary, carotid, or lower extremity artery within prior 2 years of said identification; and wherein the subject is administered said sustained release naltrexone, or a pharmaceutically acceptable salt thereof, and said sustained release bupropion, or a pharmaceutically acceptable salt thereof, in a tablet containing 8 mg of sustained release naltrexone and 90 mg of sustained release bupropion.

8. The method of claim 7, wherein said subject does not have Type 2 diabetes mellitus with at least 2 risk factors selected from the group consisting of:
- hypertension controlled with or without pharmacotherapy at <145/95 mm Hg; dyslipidemia requiring pharmacotherapy;
- documented low HDL cholesterol, <50 mg/dL in women or <40 mg/dL in men, within prior 12 months of said identification; and
- current tobacco smoker.

9. The method of claim 7, wherein the subject achieves a percentage of weight loss of at least 5%.

10. The method of claim 7, wherein administering the naltrexone and bupropion does not increase said subject's risk of an adverse cardiovascular outcome.

11. The method of claim 7, wherein said adverse cardiovascular outcome is cardiovascular death, nonfatal myocardial infarction, or nonfatal stroke.

12. A method of treating a subject at increased risk of a major adverse cardiovascular event for overweight or obesity comprising:

administering to an overweight or obese subject at increased risk of a major adverse cardiovascular event an amount of sustained release naltrexone or a pharmaceutically acceptable salt thereof in a range of about 4 mg to about 50 mg per day and an amount of sustained release bupropion or a pharmaceutically acceptable salt thereof in a range of about 30 mg to about 500 mg per day;

wherein said overweight or obese subject is at increased risk of a major adverse cardiovascular event if said subject has been diagnosed as having cardiovascular disease with at least one risk factor selected from the group consisting of:
- a history of documented myocardial infarction >3 months prior to said identification;
- a history of coronary revascularization including coronary artery bypass graft surgery, stent placement, percutaneous transluminal coronary angioplasty, or laser atherectomy;
- angina with ischemic changes, ECG changes on a graded exercise test, or positive cardiac imaging study;
- ankle brachial index <0.9 assessed by simple palpation within prior 2 years of said identification; and
- ≥50% stenosis of a coronary, carotid, or lower extremity artery within prior 2 years of said identification; and wherein said major adverse cardiovascular event is cardiovascular death, nonfatal myocardial infarction, or nonfatal stroke.

13. The method of claim 7, wherein said subject does not have Type 2 diabetes mellitus with at least 2 risk factors selected from the group consisting of:
- hypertension controlled with or without pharmacotherapy at <145/95 mm Hg; dyslipidemia requiring pharmacotherapy;
- documented low HDL cholesterol, <50 mg/dL in women or <40 mg/dL in men, within prior 12 months of said identification; and
- current tobacco smoker.

14. The method of claim 7, wherein the subject achieves a percentage of weight loss of at least 5%.

15. The method of claim 7, wherein administering the naltrexone and bupropion does not increase said subject's risk of an adverse cardiovascular outcome.

\* \* \* \* \*